(12) United States Patent
McAllister et al.

(10) Patent No.: US 11,590,330 B2
(45) Date of Patent: *Feb. 28, 2023

(54) MICRONEEDLE PATCHES AND METHODS

(71) Applicant: Georgia Tech Research Corporation, Atlanta, GA (US)

(72) Inventors: Devin McAllister, Marietta, GA (US); Mark R. Prausnitz, Atlanta, GA (US); Sebastien Henry, Smyrna, GA (US); James J. Norman, North Bethesda, MD (US)

(73) Assignee: Georgia Tech Research Corporation, Atlanta, GA (US)

( * ) Notice: Subject to any disclaimer, the term of this patent is extended or adjusted under 35 U.S.C. 154(b) by 683 days.

This patent is subject to a terminal disclaimer.

(21) Appl. No.: 16/384,665

(22) Filed: Apr. 15, 2019

(65) Prior Publication Data

US 2019/0240469 A1    Aug. 8, 2019

Related U.S. Application Data

(63) Continuation of application No. 15/025,683, filed as application No. PCT/US2014/058406 on Sep. 30, 2014, now Pat. No. 10,265,511.

(Continued)

(51) Int. Cl.
*A61M 37/00* (2006.01)

(52) U.S. Cl.
CPC . *A61M 37/0015* (2013.01); *A61M 2037/0023* (2013.01); *A61M 2037/0046* (2013.01);
(Continued)

(58) Field of Classification Search
CPC ........ A61M 37/0015; A61M 2037/003; A61M 2037/0046; A61M 2037/0053;
(Continued)

(56) References Cited

U.S. PATENT DOCUMENTS

| 4,097,943 A | 7/1978 | O'Connell |
|---|---|---|
| 6,007,836 A | 12/1999 | Denzer |

(Continued)

FOREIGN PATENT DOCUMENTS

| WO | 200035530 A1 | 6/2000 |
|---|---|---|
| WO | 2006/131931 A2 | 12/2006 |

(Continued)

OTHER PUBLICATIONS

Supplementary European Search Report and Opinion dated Apr. 24, 2017 for PCT/US0214058406 (7 pages).

(Continued)

*Primary Examiner* — Nathan R Price
*Assistant Examiner* — Justin L Zamory
(74) *Attorney, Agent, or Firm* — Eversheds Sutherland (US) LLP

(57) ABSTRACT

Microneedle patches and systems, and methods for use of such patches and systems. In one aspect, a microneedle patch is provided including a tab portion for handling the microneedle patch. In another aspect, a system is provided including a microneedle patch and a tray for housing the microneedle patch. In still another aspect, various indicators providing for providing feedback prior to, during, and after administration of the microneedle patch are provided. Advantageously, the described microneedle patches and systems provide improved handling and ease of application of the microneedle patches to skin for the delivery of therapeutic agents.

31 Claims, 10 Drawing Sheets

Related U.S. Application Data

(60) Provisional application No. 61/884,396, filed on Sep. 30, 2013, provisional application No. 62/029,202, filed on Jul. 25, 2014, provisional application No. 62/024,062, filed on Jul. 14, 2014.

(52) U.S. Cl.
CPC ............... *A61M 2037/0061* (2013.01); *A61M 2205/581* (2013.01); *A61M 2205/582* (2013.01); *A61M 2205/583* (2013.01); *A61M 2205/586* (2013.01)

(58) Field of Classification Search
CPC .. A61M 2037/0061; A61M 2037/0023; A61M 5/3157; A61M 5/16831; A61M 2205/15; A61M 2205/581; A61M 2205/582; A61M 2205/583; A61J 1/1468; H01H 2215/036; G01L 1/06; G01L 1/044; G01L 1/046; G01L 1/2231
See application file for complete search history.

(56) References Cited

U.S. PATENT DOCUMENTS

| | | | |
|---|---|---|---|
| 6,611,707 | B1 | 8/2003 | Prausnitz et al. |
| 6,656,147 | B1 | 12/2003 | Gertsek et al. |
| 6,945,952 | B2 | 9/2005 | Kwon |
| 7,516,845 | B2 | 4/2009 | Lang et al. |
| 7,918,814 | B2 | 4/2011 | Prausnitz et al. |
| 8,419,708 | B2 | 4/2013 | Tokumoto et al. |
| 9,517,205 | B2 | 12/2016 | D'hagan et al. |
| 2002/0192273 | A1 | 12/2002 | Buseman et al. |
| 2005/0137531 | A1 | 6/2005 | Prausnitz et al. |
| 2005/0228340 | A1* | 10/2005 | Cleary .............. A61M 37/0015 604/46 |
| 2007/0088248 | A1* | 4/2007 | Glenn ................. A61M 35/006 604/46 |
| 2008/0114298 | A1 | 5/2008 | Cantor et al. |
| 2008/0140049 | A1 | 6/2008 | Kirby |
| 2008/0183144 | A1 | 7/2008 | Trautman et al. |
| 2008/0213461 | A1 | 9/2008 | Gill et al. |
| 2009/0118662 | A1 | 5/2009 | Schnall |
| 2010/0256568 | A1* | 10/2010 | Frederickson .... A61M 37/0015 604/173 |
| 2010/0262081 | A1 | 10/2010 | Lee et al. |
| 2011/0152792 | A1 | 6/2011 | Takada |
| 2012/0109065 | A1 | 5/2012 | Backes |
| 2012/0200526 | A1* | 8/2012 | Lackey ............... G06F 3/04142 345/174 |
| 2013/0006187 | A1 | 1/2013 | Kobayashi et al. |
| 2013/0023749 | A1 | 1/2013 | Afanasewicz et al. |
| 2013/0158482 | A1 | 6/2013 | Davis et al. |
| 2015/0030642 | A1* | 1/2015 | Wu ...................... A61K 39/145 424/400 |

FOREIGN PATENT DOCUMENTS

| | | |
|---|---|---|
| WO | 2007/002522 A1 | 1/2007 |
| WO | 2008091602 A3 | 7/2008 |
| WO | 2009081122 A1 | 7/2009 |
| WO | 2012/122163 A1 | 9/2012 |
| WO | 2013/096026 A1 | 6/2013 |

OTHER PUBLICATIONS

International Search Report and Written Opinion dated Jan. 16, 2015 for PCT/US2014/058406 (24 pages).

* cited by examiner

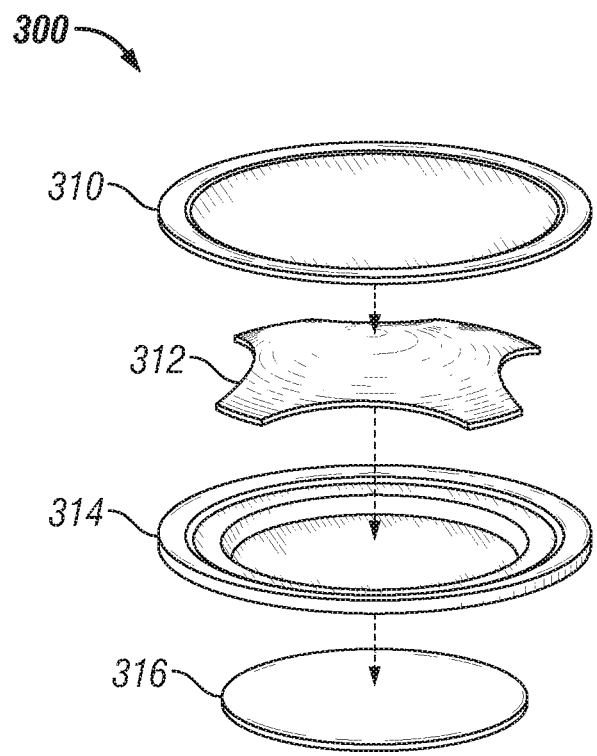
*FIG. 6A*
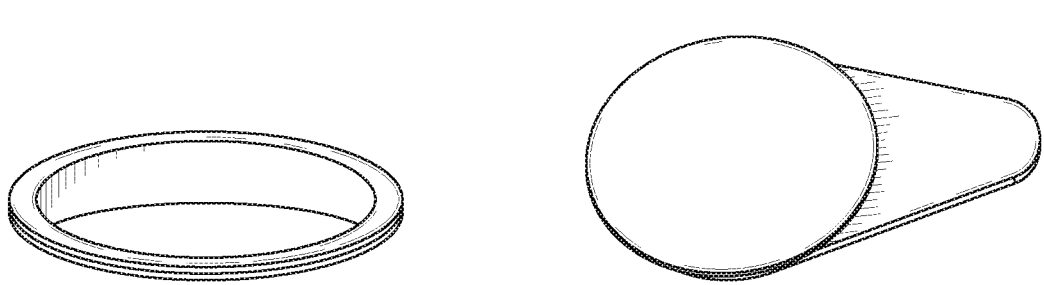
*FIG. 6B*  *FIG. 6C*

MICRONEEDLE PATCHES AND METHODS

CROSS REFERENCE TO RELATED APPLICATIONS

This is a continuation of U.S. application Ser. No. 15/025,683, filed Mar. 29, 2016, which is a national stage of PCT/US14/58406, filed Sep. 30, 2014, which claims priority to U.S. Provisional Application No. 61/884,396, filed Sep. 30, 2013, to U.S. Provisional Application No. 62/024,062, filed Jul. 14, 2014, and to U.S. Provisional Application No. 62/029,202, filed Jul. 25, 2014. All of these prior applications are incorporated herein by reference.

STATEMENT REGARDING FEDERALLY SPONSORED RESEARCH OR DEVELOPMENT

This invention was made with Government support under Contract No. EB012495 awarded by the National Institutes of Health. The Government has certain rights in the invention.

BACKGROUND

The present application is generally in the field of microneedle patches for the transport of therapeutic or biological molecules into the skin or across tissue barriers.

Transdermal drug delivery provides several advantages over other routes for administering a drug formulation to a patient. One method for transdermal drug delivery involves using microneedle arrays to bypass the barrier properties of the stratum corneum. Although microneedle arrays were first reported over 15 years ago, numerous obstacles have prolonged the development of microneedle arrays and delayed its commercialization. For example, the small size of the microneedles makes verifying effective administration of the therapeutic agents difficult. Many groups have looked to use of applicators and other types of special insertion devices that are used to apply a pre-set force that will ensure that the microneedles penetrate the stratum corneum. These applicators and other insertion devices, however, can be cumbersome to use and unnecessarily increase the cost of using the microneedle arrays.

For example, most microneedle systems under development either have separate, complex applicators or integrated applicators. The separate, complex applicators are used to handle and apply microneedle patches to the patients and can be burdensome to the user, bulky, costly for single use applications, and/or non-ideal for multi-person administration (e.g., mass vaccinations) due to cross-contamination issues. The integrated applicators are integrated into the microneedle devices themselves and become wearable systems that must be worn for the duration of the required wear time, which adds an undesirable level of 3-dimensionality to a wearable patch/device.

Other problems that have been difficult to overcome have included the scale-up of consistent and reliable methods of manufacture of microneedle arrays, development of highly concentrated and stable therapeutic agents that can be effectively administered using microneedle arrays, and cost effective systems for protecting the microneedles after manufacture until their use.

Thus, there remains a need for simple, effective, and economically desirable devices for transdermal administration of a variety of drug types to a patient.

SUMMARY

Improved microneedle patches and systems, and methods of use thereof have been developed which address one or more of the above-described needs.

In one aspect, a microneedle patch for administration of an active pharmaceutical ingredient (API) or other substance of interest into a biological tissue is provided. For example, the biological tissue may be the skin or a mucosal tissue of a human or other mammal in need of treatment or prophylaxis. The patch includes a base substrate having a microneedle side and an opposing back side with one or more solid microneedles extending from the microneedle side of the base substrate, the one or more solid microneedles including a substance of interest, such as an API. The patch further includes an adhesive layer and a handle layer affixed to the back side of the base substrate, the handle layer including a tab portion which extends away (e.g., laterally) from the one or more solid microneedles and permits a person to manually hold the tab portion (e.g., between a thumb and finger) to manipulate the patch without contacting the one or more solid microneedles.

In another aspect, a system for storing and transporting one or more microneedle patches is provided. The system includes one or more microneedle patches and a tray with an upper surface region surrounding one or more recessed regions. Each of the one or more recessed regions is dimensioned to receive in a non-contacting manner the one or more solid microneedles of a corresponding microneedle patch, with a portion of the adhesive layer of the microneedle patch being releasably secured to the upper surface region of the tray.

In yet another aspect, a microneedle patch for administration of an API or other substance of interest into a patient's skin (or into another biological tissue) including one or more feedback indicators is provided. The patch includes a base substrate having a microneedle side and an opposing back side with one or more solid microneedles extending from the microneedle side of the base substrate, wherein the one or more microneedles include the substance of interest, for example as part of the microneedle structure and/or as a coating on the microneedle structure.

In one embodiment, the microneedle patch includes a mechanical force indicator configured to provide an audible, tactile, and/or visual signal when a force applied to the patch by a user, in the course of applying the patch to a patient's skin (or into another biological tissue) to insert the one or more microneedles therein, meets or exceeds a predetermined threshold. The mechanical force indicator may be in line with and generally centered about the microneedles on the opposing back side of the base substrate.

In another embodiment, the one or more solid microneedles are dissolvable microneedles and the patch includes an indicator for providing an audible, tactile, or visual signal indicative of the one or more microneedles puncturing a patient's skin and/or completion of delivery of the substance of interest from the one or more solid microneedles in vivo following application of the patch to a patient's skin.

Methods for administering an API or other substance of interest to a patient with a microneedle patch are also provided. The methods include removing the microneedle patch from a tray in which the microneedle patch is releasably secured by manually grasping a tab portion of the microneedle patch, e.g., between the thumb and finger; applying the microneedle patch to a patient's skin; manually pressing the microneedle patch, e.g., with a finger, thumb, or heel of hand, to apply a pressure sufficient to insert the one or more microneedles into the patient's skin, and removing the microneedle patch from the patient's skin by grasping the tab portion of the microneedle patch between the thumb and finger. Similar steps could also be used to apply the patch to a biological tissue other than the skin.

Additional aspects will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

FIG. 6A is an exploded perspective view, and FIG. 6B is an assembled perspective view, of a mechanical force indicator in accordance with one embodiment of the present disclosure. FIG. 6C is a perspective, top view of the mechanical force indicator affixed to a microneedle patch in accordance with one embodiment of the present disclosure.

DETAILED DESCRIPTION

Improved microneedle patches and systems have been developed. In embodiments, the systems provide a microneedle patch which is simpler in design and ease of use. The systems provide improved handling and ease of application of the microneedle patches, e.g., to the skin of a patient, in a way that insures the proper microneedle insertion without resort to complex applicator systems.

Unless otherwise defined herein or below in the remainder of the specification, all technical and scientific terms used herein have meanings commonly understood by those of ordinary skill in the art to which the present invention belongs. It is also to be understood that the terminology used herein is for the purpose of describing particular embodiments only, and is not intended to be limiting. In describing and claiming the present invention, the following terminology will be used in accordance with the definitions set out below.

As used in this specification and the appended claims, the singular forms "a", "an," and "the" include plural referents unless the content clearly dictates otherwise. Thus, for example, reference to "a component" can include a combination of two or more components; reference to "a buffer" can include mixtures of buffers, and the like.

The term "about", as used herein, indicates the value of a given quantity can include quantities ranging within 10% of the stated value, or optionally within 5% of the value, or in some embodiments within 1% of the value.

Figure 14A:
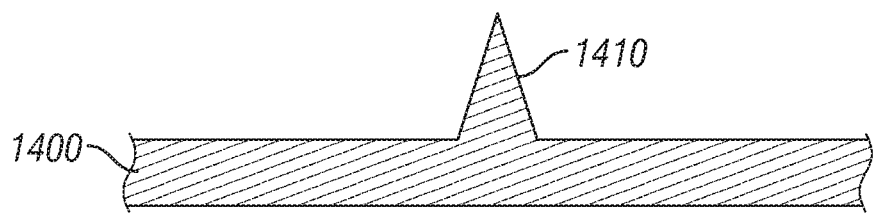
FIG. 14A is a partial cross-sectional view of an uncoated microneedle.
Figure 14B:
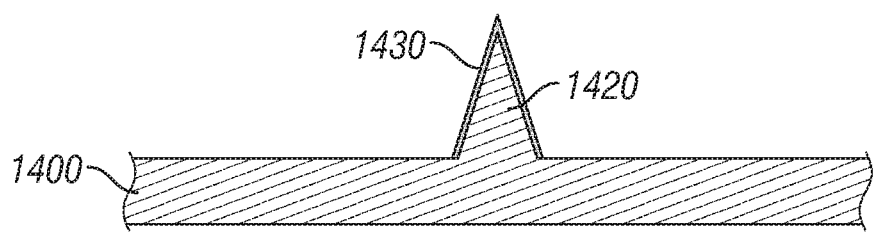
FIG. 14B is a partial cross-sectional view of a coated microneedle.

Embodiments of the present application include microneedle patches and systems having features to improve handling and use of the microneedle patches. Generally described, microneedle patches include a base substrate with one or more microneedles extending from the base substrate. In a preferred embodiment, the microneedle patch includes an array of several microneedles, e.g., from 10 to 1000 microneedles. In a preferred embodiment, the microneedles are solid microneedles that include a substance of interest, such as an active pharmaceutical ingredient (API), which becomes solubilized in vivo following insertion of the microneedle into a biological tissue, e.g., into the skin of a patient. For example, the substance of interest may be mixed into a water soluble matrix material forming the solid microneedle 1410 extending from a base substrate 1400 (FIG. 14A), or the substance of interest may in the form of a coating 1430 on a microneedle sub-structure 1420 extending from a base substrate 1400 (FIG. 14B). In either case, the substance of interest is provided in a formulation referred to herein as being "dissolvable." In embodiments in which the substance of interest and a matrix material in which the substance of interest is dispersed form the structure of the microneedle, the matrix material also preferably is dissolvable in vivo, such that the entire portion of the microneedle inserted into the biological tissue dissolves in vivo (e.g., about 90 to about 95% of the total length of the microneedle). In embodiments in which the substance of interest is part of a coating on a microneedle substructure, the substructure may also be dissolvable in vivo, but it is not required.

In embodiments, the one or more microneedles have a height from about 100 μm to about 2000 μm, from about 100 μm to about 1500 μm, from about 100 μm to about 1000 μm, or from about 500 μm to about 1000 μm. The one or more microneedles may be arranged on a base substrate in any suitable density. For example, a plurality of microneedles may be arranged in even or staggered rows in an array, wherein each microneedle is separated from its nearest neighboring microneedle by a distance between about 50% and about 200% of the height of the microneedle, (e.g., between about 75% about and about 150% of the height of the microneedle, or by about equal to the height of the microneedle). Any suitable number of microneedles may be used. In one embodiment, a plurality of microneedles may include from 5 to 10,000 microneedles, such as from 50 to 1000 microneedles or from 50 to 200 microneedles.

Microneedle Patches

Figure 1A:
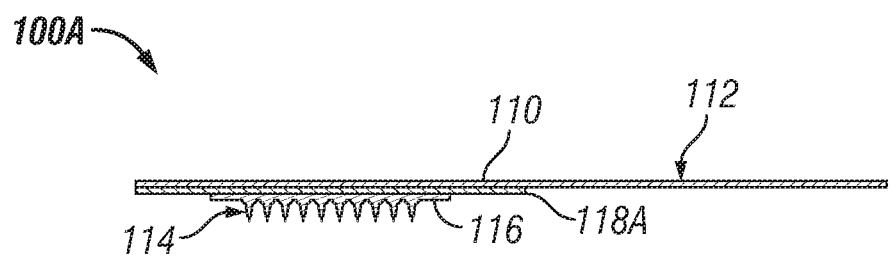
FIGS. 1A, 1B, and 1C are cross-sectional views of microneedle patches and systems according to some embodiments of the present disclosure.

An exemplary microneedle patch with a plurality of solid microneedles is illustrated in FIG. 1A. The patch 100 includes a base substrate 116 with a plurality of microneedles 114. The plurality of microneedles 114 may be affixed to a backing layer 110 by an adhesive layer 118 disposed between the backing layer 110 and the back side of the base substrate 116. In some embodiments, the backing layer 110 may include a tab portion 112 which extends away from the plurality of microneedles 114. Alternatively, the tab portion may be disposed in a separate layer (not shown). Thus, the tab portion may be in the same plane or a different plane than the backing layer. For example, in FIG. 1A the tab portion 112 extends laterally away from the plurality of microneedles 114. The "backing layer" and "handle layer" may be used interchangeably in the present disclosure unless expressly provided otherwise.

The tab portion 112 advantageously enables a patient or caregiver to handle the patch without contacting the "body portion" of the patch defined by the base substrate 116 and plurality of microneedles 114, thereby beneficially reducing the potential of contaminating or damaging the plurality of microneedles 114 and eliminating unwanted contact with the adhesive layer. For example, the tab portion 112 may be sized and shaped to permit a person to manually hold the tab portion 112 (e.g., between a thumb and finger). Although the tab portion 112 is illustrated in FIG. 1A as extending laterally asymmetrically from the body portion, other shapes and sizes also are envisioned. For example, the tab portion may be about the same size as the body portion, larger than the body portion, or smaller than the body portion. In some embodiments, the tab portion may extend laterally from all sides of the body portion. The size of the tab portion may be at least in part dictated by the material used to make the tab portion (e.g., depending on its stiffness and the like).

The backing layer may be made out of a variety of materials, and may be the same or different than the tab portion. In some embodiments, the backing layer may be a composite material or multilayer material including materials with various properties to provide the desired properties and functions. For example, the backing material may be flexible, semi-rigid, or rigid, depending on the particular application. As another example, the backing layer may be substantially impermeable, protecting the one or more microneedles (or other components) from moisture, gases, and contaminants. Alternatively, the backing layer may have other degrees of permeability and/or porosity based on the desired level of protection that is desired. Non-limiting examples of materials that may be used for the backing layer include various polymers, elastomers, foams, paper-based materials, foil-based materials, metallized films, and non-woven and woven materials.

The backing layer 110 may be temporarily or permanently affixed to the base substrate 116 by the adhesive layer 118. In some embodiments, the adhesive layer may be disposed primarily in the body portion of the patch between the base substrate 116 and backing layer 110. For example, the adhesive layer 118 may be disposed between the base substrate 116 and backing layer 110, and may extend beyond the base substrate 116 to help adhere the patch to the patient's skin during application. The portion of the adhesive layer extending beyond the base substrate also may function to adhere the patch to a tray or container covering the plurality of microneedles during shipping and storage, as well as for disposal after its use.

Figure 1B:
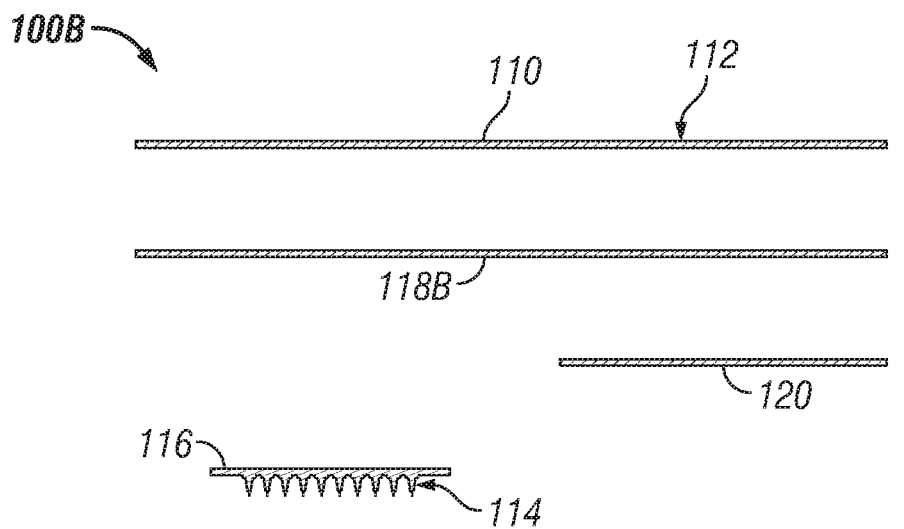

In a preferred embodiment, as illustrated in FIG. 1A, the tab portion 112 is substantially free of the adhesive layer, enabling a person handling and applying the patch to do so without contacting the adhesive layer 118A. In some embodiments, as illustrated in FIG. 1B, the adhesive layer 118B may be disposed over substantially all of a side of the backing layer 110, including the tab portion 112. A cover portion 120 may be disposed over the adhesive layer 118 over the tab portion 112 so that a person holding the patch by the tab portion does not contact much or any of the adhesive layer.

In some embodiments, the adhesive layer 118 is a differential adhesive. As used herein, a "differential adhesive" may have a different coefficient of adhesion between various types of substrates. For example, a differential adhesive may have a coefficient of adhesion between the base substrate and the backing layer greater than the coefficient of adhesion between the backing layer and the patient's skin. Similarly, the coefficient of adhesion between the base substrate and the backing layer may be greater than the coefficient of adhesion between the backing layer and the tray or container in which it is stored. The coefficient of adhesion between the backing layer and the tray or container in which it is stored may be greater or less than the coefficient of adhesion between the backing layer and the patient's skin.

By having differential degrees of adhesion, the patch can be removed from the tray or container relatively easily, adhered to the skin firmly, and removed from the skin when administration is complete, while still keeping the base substrate affixed to the backing layer throughout its use. Such differential adhesion also may be obtained by using more than one type of adhesive (e.g., a first adhesive between the base substrate and backing layer and a second adhesive beyond the base substrate and backing layer), modifying the amount, thickness, and/or pattern of adhesive that is applied, or using a coating/release liner or other features to modify the coefficient of adhesion.

In some embodiments, the backing layer may include a label disposed on the back side of the backing layer opposite the adhesive layer. The label may be printed directly onto the backing layer or attached to the backing layer. Such a label may be used to provide various types of information useful to the caregiver and/or patient. For example, the label may provide an API identity and dosage in the patch, product serial number or batch information, instructions for administration, expiration date, and the like. In some embodiments, the label may be incorporated directly into a handle layer that is distinct from the backing layer.

Microneedle Patch Storage System

Figure 1C:
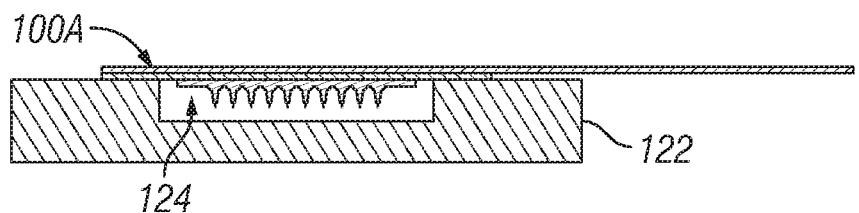

Turning back to FIG. 1C, the microneedle patch 100 may be housed on a tray 122 having an upper surface region surrounding one or more recessed regions 124. The one or more recessed regions 124 may be dimensioned to receive in a non-contacting manner the one or more microneedles 114 of a corresponding microneedle patch 100, with the adhesive layer of the microneedle patch being releasably secured to the upper surface region of the tray. Because contact between the tray and microneedle patch is limited substantially to the adhesive layer and/or backing, the integrity of the one or more microneedles is advantageously retained during storage. In addition, the tray may also protect the one or more microneedles from moisture, gases, or other contaminants that could degrade the substance of interest, reduce the shelf life, or diminish the effectiveness of the substance of interest.

Figure 3A:
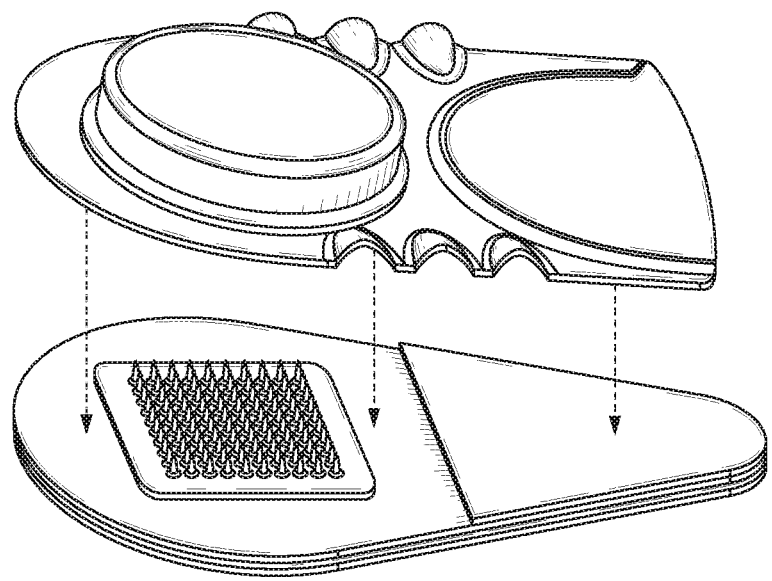
FIG. 3A is an exploded, perspective view.
Figure 3B:
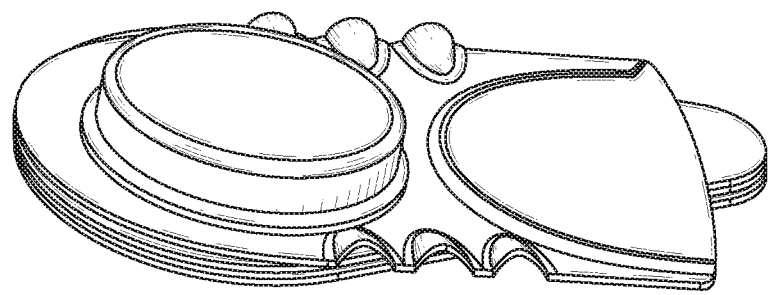
FIG. 3B is an assembled perspective view, of a microneedle system in accordance with one embodiment of the present disclosure.
Figure 4A:
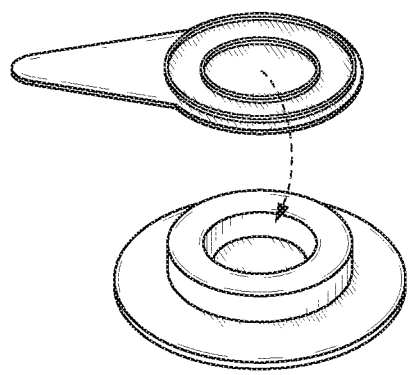
FIG. 4A is an exploded, perspective view.
Figure 4B:
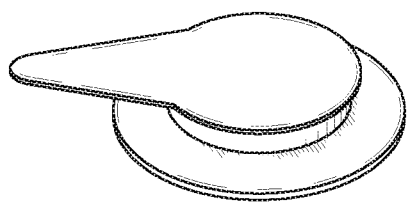
FIG. 4B is an assembled perspective view, of a microneedle system in accordance with another embodiment of the present disclosure.
Figure 5A:
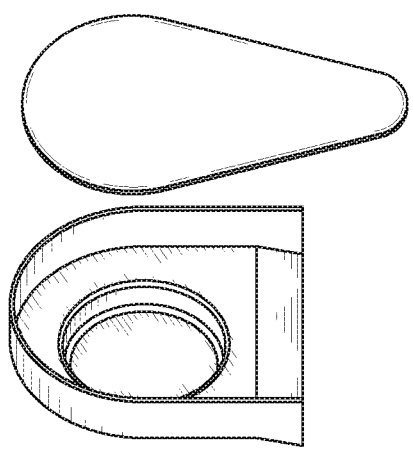
FIG. 5A is an exploded, perspective view.
Figure 5B:
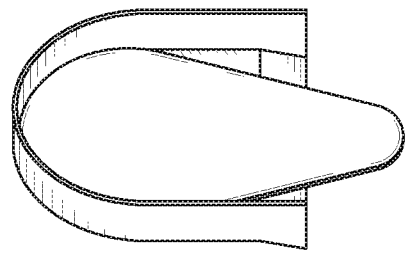
FIG. 5B is an assembled perspective view, of a microneedle system in accordance with still another embodiment of the present disclosure.
Figure 13A:
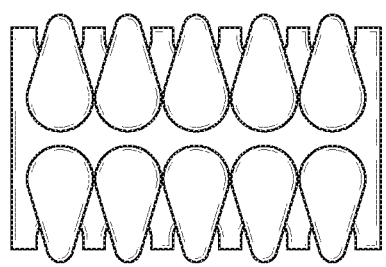
FIGS. 13A-D are schematics illustrating a process for using a microneedle system in accordance with one embodiment of the present disclosure of administering a microneedle patch to a patient.
Figure 13B:
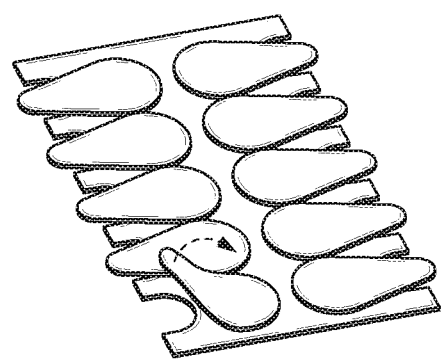
Figure 13C:
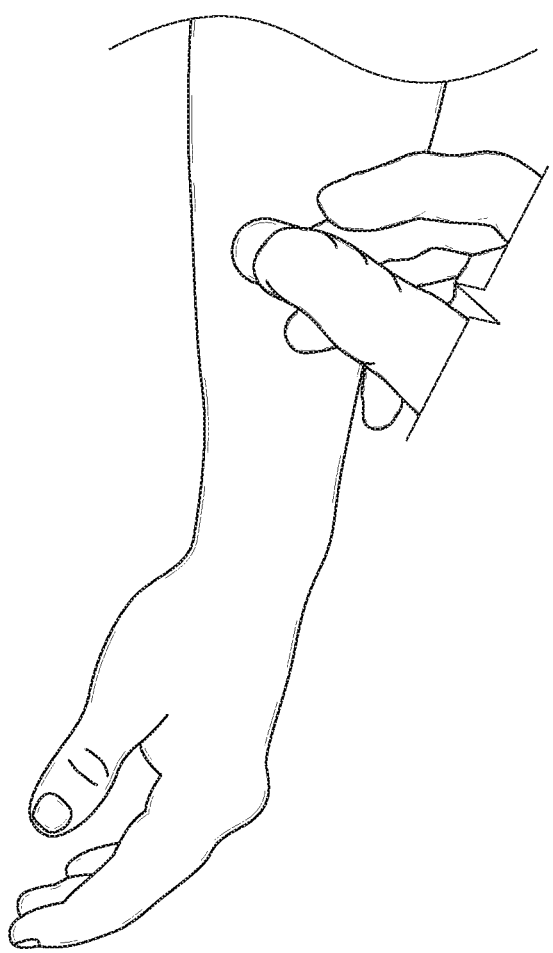
Figure 13D:
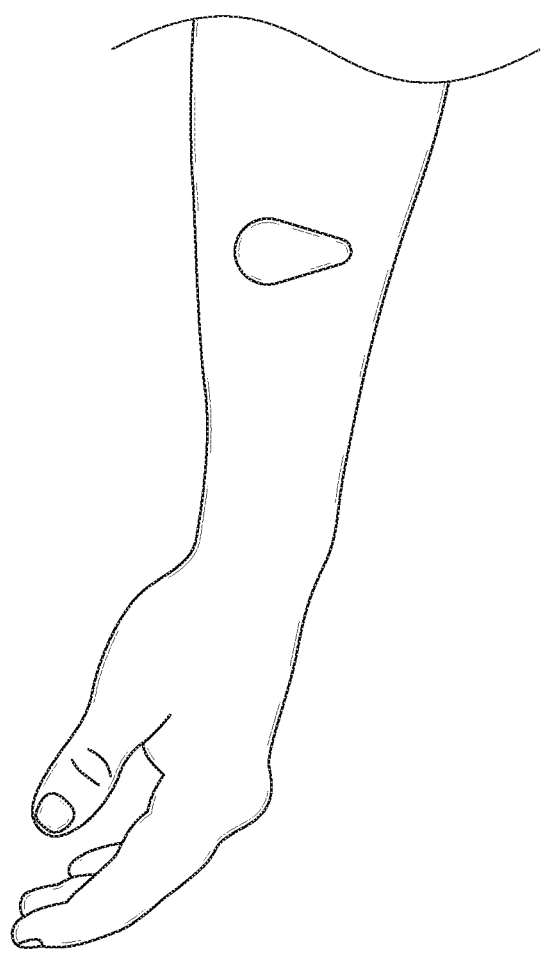

The trays may take a variety of shapes and sizes, such as the rectangular shape illustrated in FIGS. 3A-B, the planar shape with a formed cap illustrated in FIGS. 4A-B, or the partial ellipsoidal shape illustrated in FIGS. 5A-B. The tray may further include one or more additional features with various functions or to impart a desired aesthetic to the tray. For example, the tray may include one or more depressions (FIGS. 3A-3B), holes, or cutouts (FIGS. 13A-B). Such features may facilitate removal of the microneedle patch from the tray. The recessed region for receiving the one or more microneedles also may be positioned in the tray such that at least a portion of the tab extends over the perimeter of the tray (FIGS. 3B, 4B, 5B).

A variety of materials may be used to make the trays provided herein, non-limiting examples of which include polymers (e.g., polytetrafluoroethylene (PTFE), fluorinated ethylene propylene (FEP), polyvinylidene fluoride (PVDF), polyvinyl fluoride (PVF), polyethylene, or polypropylene), metallized polymers, elastomers, non-woven and woven materials, paper-based materials, foam, metal or foil, and the like. In some embodiments, the tray may be formed of composite materials or multilayer materials. For example, a multilayer material may include one or more layers that impart the desired structural properties and one or more layers that impart the desired barrier properties.

In one embodiment, the tray includes a coating on one or more surfaces of the tray. For example the tray may include coatings that provide moisture and gas barrier properties to the recessed region where the one or more microneedles are contained, coatings that include desiccant, or coatings that facilitate release of the microneedle patch from the tray (e.g., a release liner or the like). For example, the tray may be coated with a material (e.g., silicone, oils, wax, PTFE) that has a low surface energy (e.g., ≤30 dynes/cm, preferably ≤20 dynes/cm) so that the patch can be readily peeled off of the tray. The tray also may include certain surface patterns or textures (e.g., bumps, ridges, holes, etc.) that reduce the contact area between the adhesive layer and the tray to further aid removal of the patch from the tray. The tray also may include one or more nesting features (e.g., matingly dimensioned raised and recessed areas) that facilitate stacking of multiple trays.

A tray may be configured to house a single patch or a plurality of patches (e.g., 2, 3, 4, 5, 6, 7, 8, 10, 12, or 20 patches, or more or less). FIGS. 13A-B illustrates a tray having 10 microneedle patches stored in two rows of five. In one embodiment, the tray includes a plurality of recesses, with each recess corresponding to one of the microneedle patches. The trays also may include one or more lines of weakness (e.g., perforations, score lines, and the like) so that portions of the tray are separable from other portions of the tray. In some embodiments, the patches may be stored on only one side of the tray, while in other embodiments, the patches may be stored on both sides of the tray (e.g., with recessed regions on both sides of the tray). In still other embodiments, the tray may have a three-dimensional geometry, such as a cube, with recessed regions for housing the patches on all sides (e.g., six sides for the cube). Thus, the trays may be designed such that a plurality of patches may be efficiently stored (e.g., the center-to-center spacing of the recessed regions may be approximately equal to the center-to-center spacing of the patches) such that a majority of the tray surface is covered by patches.

These trays, together with the patch, may alone be sufficient to protect the microneedle patch prior to use; however, additional features also may be used. For example, one or more trays may be disposed in a flexible container (e.g., pouch) and/or rigid container (e.g., box). In some embodiments, a lid may be disposed on the tray to protect the microneedle patch prior to use. Such lids may be the same or a different material from the tray, and may be sealed to the perimeter of the tray (i.e., using a heat seal, cold seal, or pressure sensitive adhesive). In one embodiment, a desiccant may be provided in the recessed regions or in the flexible or rigid container housing the tray. A desiccant may alternatively or in addition be part of the tray itself. For example, a desiccant material may be included (e.g., dispersed in or coated onto) the material forming the structure of the tray. For example, the tray may be formed of a desiccant polymer known in the art.

In addition to the protective function prior to use, the trays provided herein also improve ease of handling of the microneedle patches and require less material than other types of microneedle patch packaging, thereby reducing both cost of handling and materials.

Moreover, the trays also may be used for disposal of a used microneedle patch by applying the patch to the tray such that the remaining one or more microneedle substructure, any residual substance of interest, or biological waste is contained within the recessed region.

The trays may be formed using a variety of different methods, non-limiting examples of which include various molding methods (e.g., thermoforming, injection molding, stamping, casting), 3-D printing, machined, laser sintered, and the like. In embodiments in which the tray houses a plurality of microneedle patches, it may be desirable to manufacture the microneedle patches in multi-patch cards or webs. In this way, the multiple patches are all attached to each other at one point during the manufacturing process, and may be configured such that the geometry of the microneedle patches during manufacture matches the configuration in which the microneedle patches are disposed on the tray. During the manufacturing or subsequently, a plurality of microneedle patches may be applied substantially simultaneously to the tray. In some embodiments, one multi-patch card may be applied per tray. Alternatively, a plurality of multi-patch cards may be applied per tray. After application of the multi-patch card to the tray, the backing layer of the patches may be weakened (e.g., perforated, scored, or cut) so that the patches are no longer contiguous or are easily separable by a user. In some embodiments, the microneedle patches may be formed by a molding process using a mold that also functions as the tray or as a component of the tray. In such instances, the microneedles would not require removal from the mold during the manufacturing process and could instead be removed from the mold prior to application by a user.

Feedback Indicators

In another aspect, various indicators are provided with the microneedle patches. The indicators provide a mechanism for providing a user with feedback to assist with the proper and effective use of the microneedle patch. The feedback may be provided in a variety of forms or combinations, including visual (e.g., change in color or other physical appearance of the patch), tactile (e.g., a detectable sensation felt by the person administering the patch or patient), audible (e.g., the presence, absence, or change of sound), olfactory (e.g., a release of a fragrance upon dissolution of the microneedles or upon wetting of the patch), gustatory (e.g., a change of taste observed by licking the patch backing layer until a specific taste is detected or observed in application of the patch to mucosal tissue (e.g., for treatment of a dental condition or for a mucosal vaccination), such as sweet, salty, sour, or bitter). Alternatively, the feedback may be indirect and then converted into such a signal, or may be converted between different types of signals (e.g., an electronic communication transmitted to an electronic device, such as a computer, tablet, or smart phone).

The indicators generally may be characterized as having an initial configuration before providing the feedback signal, and a signaling configuration which differs from the initial configuration and which provides the feedback signal. In some embodiments, the signaling configuration is reversible, such that the indicator may return to its initial configuration after providing the feedback signal. In other embodiments, the indicator assumes a third configuration (i.e., different from the initial configuration and different from the signaling configuration) after providing the feedback signal.

The feedback may be provided to a variety of "users", including the patient or a person or an organization other than the patient (e.g., a health care worker, caregiver, parent, guardian, patch manufacturer/supplier, regulatory agency, insurance company, and the like). In some instances, the feedback may be provided to a remote device that interacts with the microneedle patch (e.g., an electronic controller) by receiving feedback and providing output in response to directly alter the operation of the microneedle patch or to provide information to a person who can use that output information, potentially to alter microneedle patch operation.

Application Force/Pressure

In a preferred embodiment, the feedback indicator is or includes a mechanical force indicator that can be used to indicate to the user the amount of force and/or pressure applied to the patch during its administration. For example, in one embodiment, the indicator is configured to provide a signal when a force applied to the patch by a user (in the course of applying the patch to a patient's skin to insert the one or more microneedles into the patient's skin) meets or exceeds a predetermined threshold. The predetermined threshold is the minimum force or some amount greater than the minimum force that is required for a particular microneedle patch to be effectively applied to a patient's skin. That is, it is the force needed to cause the microneedles to be properly, e.g., fully, inserted into a patient's skin.

The mechanical force indicator can signal to the user in a variety of different ways that the predetermined threshold has been met or exceeded. In one embodiment, the mechanical force indicator may change from its initial configuration to its signaling configuration upon receiving a force which meets or exceeds the predetermined threshold.

In advantageous embodiments, the microneedle patch is configured such that the microneedles will properly penetrate the patient's skin before the mechanical force indicator changes to its signaling configuration. That is, the patch can be properly applied independently of operation of the mechanical feedback indicator. In contrast, certain conventional microneedle patches require some type of patch deformation to occur before the microneedles are inserted into the skin.

In one embodiment, the mechanical force indicator operates based on material deformation or fracture of a component of the indicator. For example, a structural feature may deform or fail once the predetermined threshold force is met or exceeded. Such a deformation or failure may be complete or partial. In different embodiments, the deformation may be plastic or elastic; it may be reversible or irreversible. Non-limiting examples of materials that undergo such deformation include metals, polymers, viscoelastic materials, bi-phasic materials, and the like. The mechanical force indicator may include one or more springs.

Figure 7:
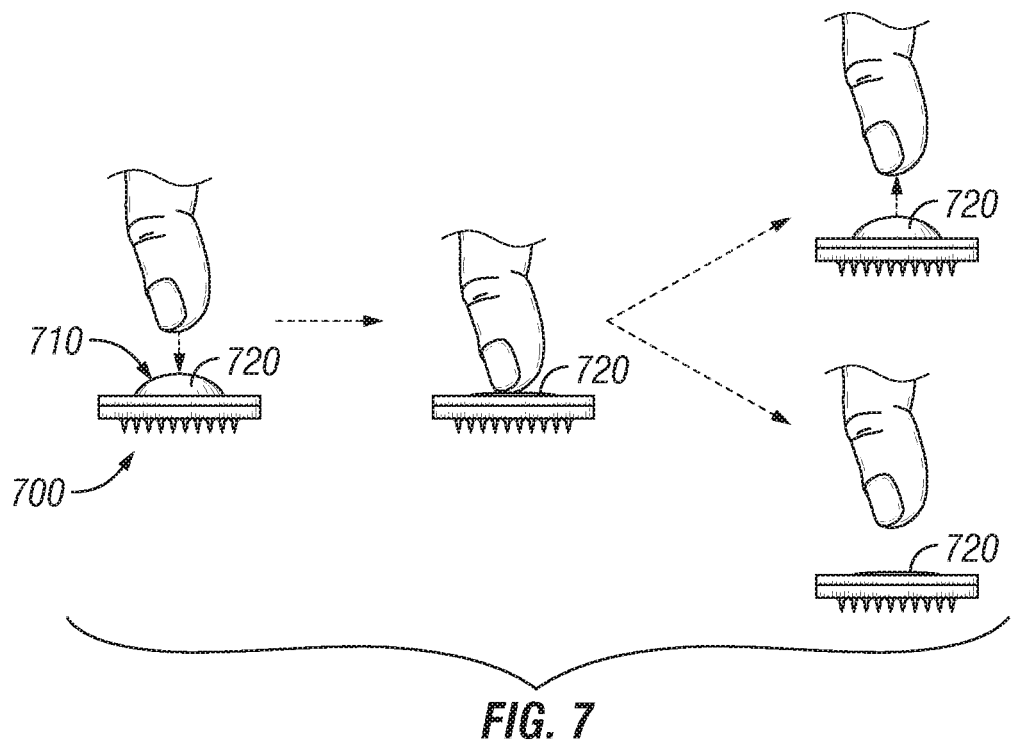
FIGS. 7-12C are schematics illustrating the operation and use of various feedback indicators associated with a microneedle patch, in accordance with several different embodiments of the present disclosure.

One embodiment of a mechanical force indicator that undergoes material deformation or failure is shown in FIG. 7. Here, the microneedle patch 700 includes a mechanical force indicator 710 attached to an upper surface of the patch (opposite side from the microneedles). The indicator 710 includes a snap dome 720, which may be a bi-phasic material. The snap dome is designed to collapse (deform) upon application of a sufficient force, which meets or exceeds the predetermined threshold. Upon removal of the force, the bi-phasic material may remain partially or completely deformed or may substantially return to its original curved shape. Advantageously, the collapse may emit a snapping sound, is clearly visible, and/or can be felt by the user's finger used to apply the patch. In this way, the snap dome provides tactile, visual, and audible signals to the user that the threshold force is met or exceeded and that the patch has been properly applied to the patient's skin.

As used herein, "bi-phasic material" refers to a material that does not deform continuously under pressure, but rather adopts one shape in its initial configuration and another shape in its signaling configuration. An exemplary type of bi-phasic material is a "snap dome" or "button", which consists of one or more parts that deform under pressure. For example, snap domes having a single non-planar part may remain whole after deformation or break and separate into two or more parts after deformation. Alternatively, snap domes having two or more parts may become joined together to form a single part after enough pressure has been applied (e.g., a snap having a male part and a female part). A particular snap dome may be selected such that the actuation force required to deform the snap dome is equal to or higher than the predetermined threshold force required for effective microneedle insertion.

Figure 2A:
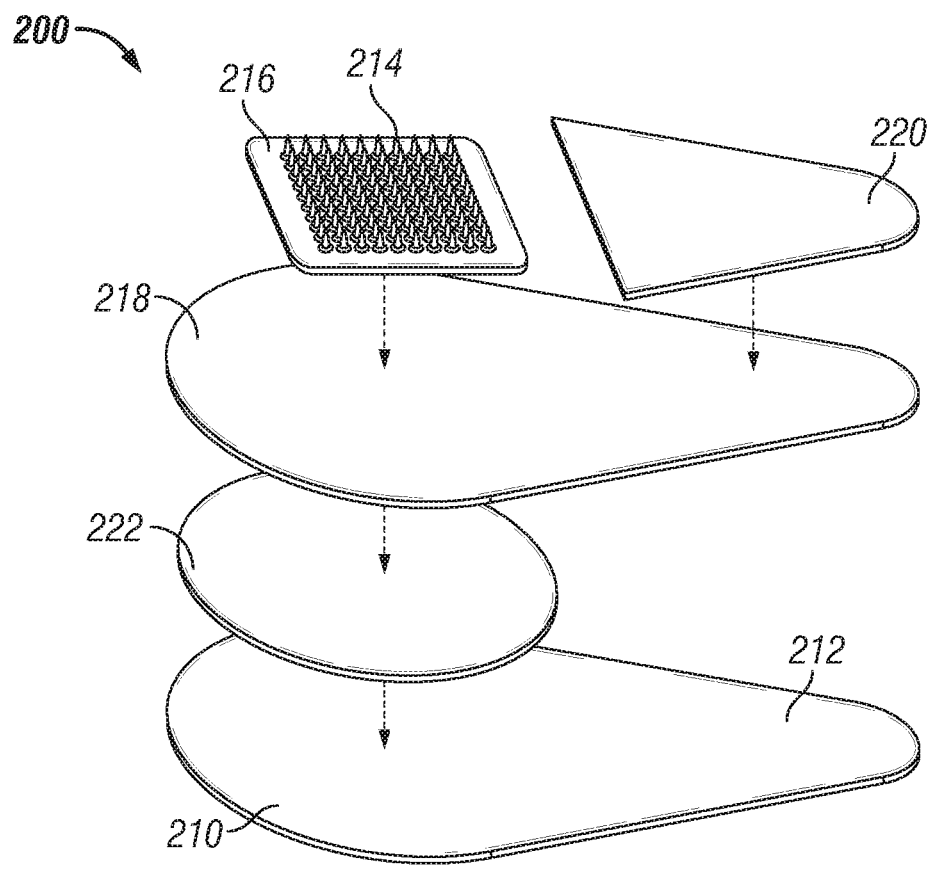
FIG. 2A is an exploded, perspective view.
Figure 2B:
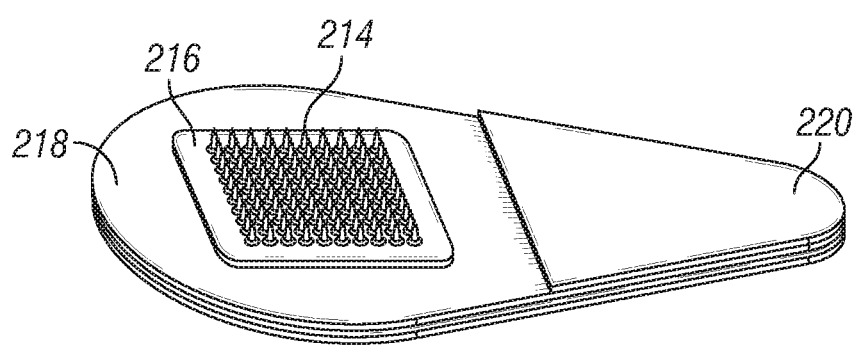
FIG. 2B is an assembled perspective view, of a microneedle patch in accordance with one embodiment of the present disclosure.

Two exemplary mechanical force indicators comprising snap domes are shown in FIG. 2A and FIGS. 6A-6C. In FIG. 2A, a microneedle patch 200 includes a microneedle array 214 on a base substrate 216. The microneedle array 214 is affixed to a backing layer 210 including a tab portion 212 by an adhesive layer 218. An adhesive cover 220 is disposed on the portion of the adhesive layer 218 over the tab portion 212. A mechanical force indicator 222 is disposed between the adhesive layer 218 and backing portion 210. The mechanical force indicator 222 may be a non-planar disc or dome that deforms upon application of the threshold force. In FIGS. 6A-6B, the indicator 300 includes a non-planar disc 312 disposed in its own housing formed by a disc-shaped tray 314 and a backing material 310. The disk may be constructed of a suitable metal or polymer. An adhesive layer 316 may be used to affix the indicator 300 onto either the opposing back side of the backing layer (FIG. 6C) or the base substrate (not shown).

In another embodiment, the mechanical force indicator includes a viscoelastic material. Such materials may be selected based on the desired stiffness or Young's modulus, so that the force required to deform the materials (i.e., fully or partially compress in this instance) is equal to or higher than the predetermined threshold force required to verify proper microneedle insertion. Non-limiting examples of viscoelastic materials that may be used include foams (e.g., polyurethane, silicone, polyethylene, nitrile), elastomers (e.g., polyurethane, silicone, nitrile, butyl, polyacrylic, fluoroelastomers), and other viscoelastic materials known in the art.

In still another embodiment, the mechanical force indicator may include a spring. For example, a spring may be selected with a desired combination of spring rate and deflection length. The more force required, the higher the spring constant and/or greater deflection length of the spring. Thus, the spring and its rate may be selected such that the force required to fully or partially compress the spring is equal to or higher than the predetermined threshold force. The spring may be in the form of a compression spring consisting of a coiled wire (most commonly with a circular cross-section, but other wire cross-sections may be desirable including square, rectangular, oval, etc.) with a constant diameter or cross-sectional dimension, or may be a conical spring or tapered spring (e.g., with a tapering diameter).

Conical springs may be compressed flat and have a relatively uniform rate constant throughout its entire deflection length (unlike standard compression spring rate constants that increase rapidly toward the maximum deflection length). With any of the foregoing springs, it may be desirable to mechanically maintain the spring in a substantially-compressed state to provide a thinner initial spring mechanism in order to provide a lower profile patch (i.e., flatter); however, other types of springs that are flatter and provide the desired feedback through a very small total deflection may be desirable. Non-limiting examples of flat springs include finger springs, disc or washer springs, wave springs, and the like. Springs are commonly made from metals or alloys (e.g., spring and stainless steels), but can also be made from plastics, elastomers (e.g., urethane springs, which are generally tubular in shape), and other materials. A spring-like effect also can be obtained using a gas in a sealed compartment (i.e., a gas spring), the deflection of which may be reversible or irreversible. For example, a plastic blister (or balloon) filled with air compresses when pressed on. Once the desired predetermined threshold force is applied, the blister will pop due to material failure under pressure, thereby providing the user with tactile, audible, and/or visual signals.

The foregoing mechanical force indicators may be reversible or irreversible (e.g., as determined by whether it can return to its initial configuration after changing to its signaling configuration). For example, in the case of a spring or viscoelastic material, the spring or viscoelastic material may regain its initial shape. However, such indicators also can be configured to undergo irreversible deflection or displacement by integrating them with other components, such as snap-in-place mechanism where the spring becomes stuck within another part or where two separate parts latch together (e.g., finger-ledge mechanism, snap mechanism, hook and loop, pressure sensitive tape, press-fit held in place by interference friction, magnetic) when the spring and other material are fully engaged. In the case of material failure (e.g., by fracture), the change will be irreversible. The indicator may also be partially reversible, in which the indicator partially, but not fully, returns to its initial configuration.

Still other types of mechanical force indicators may be used to indicate when a predetermined threshold force is applied to the microneedle patch. For example, the mechanical force indicator may cause a detectable change to one or more materials that are an integral part of or attached to the backing layer of the microneedle patch. Non-limiting examples of such detectable changes include changes in color or color intensity, wetness appearance, texture, and/or temperature. One such material change may be provided by a surface pressure-indicating film that reveals pressure distribution and magnitude by virtue of a color change or color intensity change. Another exemplary material is one that may deform when pressed on by the finger or thumb during its administration to a patient's biological tissue and retains, either permanently or temporarily, the finger/thumb imprint (e.g., such as the above-described viscoelastic materials). Yet another exemplary material is one that which, when compressed, makes a sound (e.g., as a result of air being forced out of the material or as a result of friction between objects such as beads or pellets contained within the material).

Figure 8:
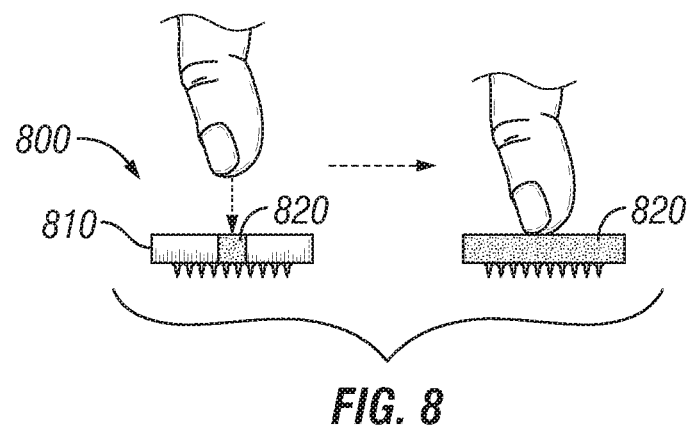

FIG. 8 illustrates one embodiment of a feedback indicator based on visual color cues. In this embodiment, the feedback indicator includes a dye or ink 820 that is contained within a reservoir (e.g., such as a blister or capsule that breaks upon application of a given force and releases the dye) in the backing layer 810 (or another layer) of the microneedle patch 800. Upon meeting or exceeding the threshold force, the dye 820 is released from the reservoir so that a change of color is observable in at least part of the patch. In one embodiment, illustrated in FIG. 8, the dye 810 is released into the backing layer 810 or another layer of the microneedle patch, providing a visual signal that a sufficient force was applied. In another embodiment, the dye is transferred from the reservoir to the finger or thumb of the person applying the microneedle patch to the patient. In still another embodiment, the dye diffuses from one portion of the patch to another portion of the patch. The diffusion of the dye within the patch also may act as an indicator of the wear time of the patch.

Figure 10:
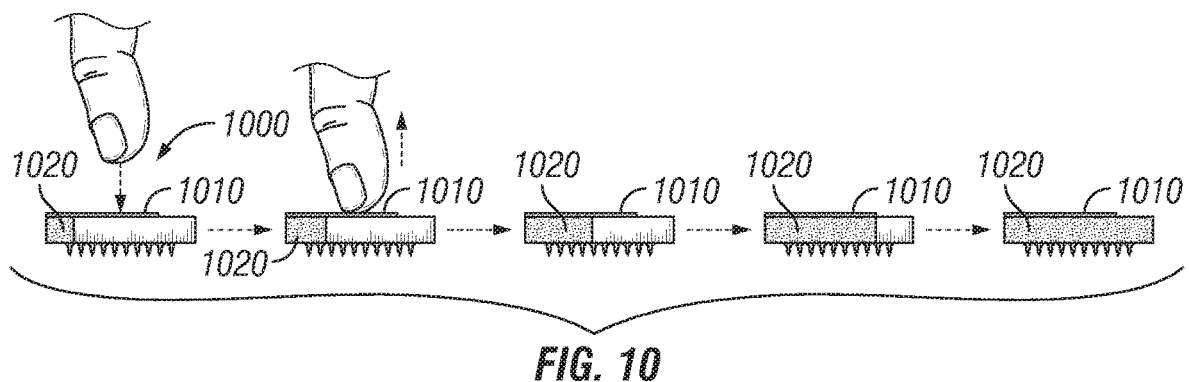

FIG. 10 illustrates another embodiment of a feedback indicator based on visual color cues. In this embodiment, diffusion of a dye from one area of the patch to another area of the patch occurs after the predetermined threshold force is applied to the microneedle patch. The microneedle patch 1000 includes a dye 1020 located in a portion of the patch beneath an opaque barrier 1010 attached to an upper surface of the patch (opposite side from the microneedles). Upon application of the predetermined threshold force, the dye 1020 begins to move to another portion of the patch. After a period of time, the dye 1020 reaches another portion of the patch that is not covered by an opaque barrier 1010 so that it can be seen by a user, thereby providing an indication that the patch has been applied to the patient's biological tissue, such as the skin, for a sufficient amount of time to ensure release of the substance of interest (e.g., a therapeutically effective amount of the API).

Figure 12A:
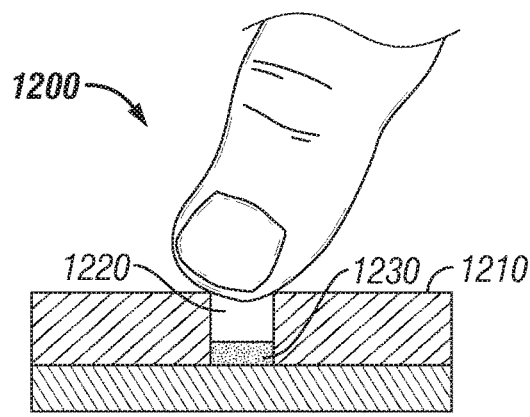
Figure 12B:
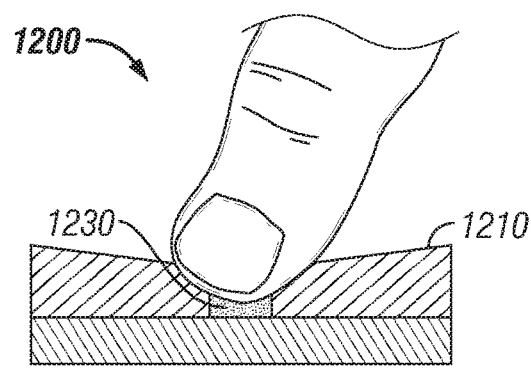
Figure 12C:
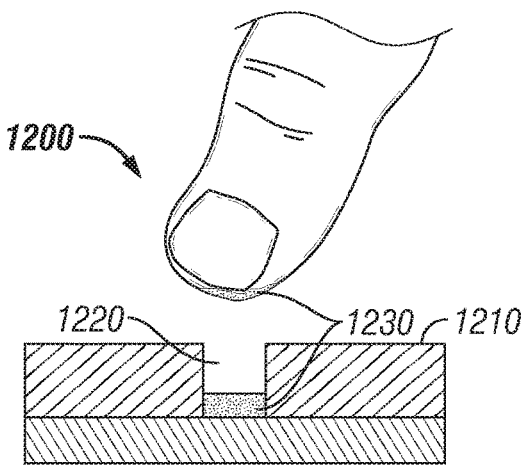

FIGS. 12A-12C illustrates yet another embodiment of a feedback indicator using dye movement. In this embodiment, a dye 1230 is provided in the microneedle patch 1200 in a recessed portion 1220 of indicator structure 1210 and then contacts the finger or thumb of a user applying pressure to the patch only when the force applied by the user reaches or exceeds the predetermined threshold force. That is, the application force must meet or exceed the predetermined threshold force in order to sufficiently compress the indicator structure 1210 defining the recessed portion 1220 containing the dye 1230, so as to permit the finger or thumb to contact the dye 1230.

Figure 11:
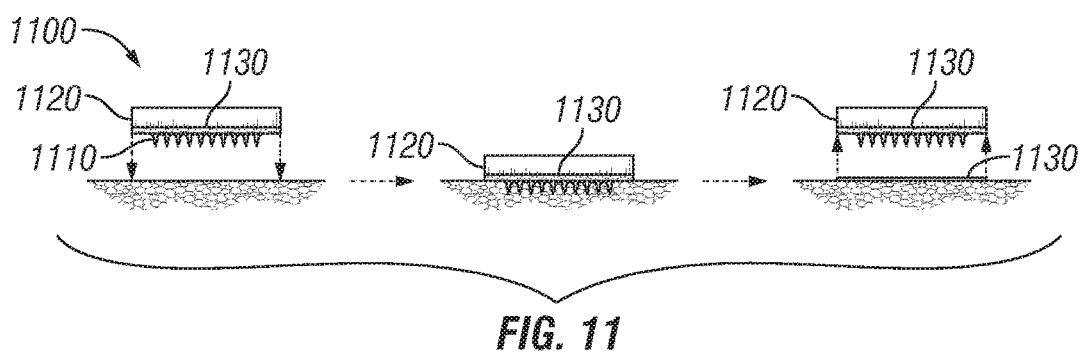

In another embodiment, a porous material, such as a sponge, contains a dye that, upon application of the predetermined threshold force, releases the dye. In still another embodiment, a material is coated with a dye that is transferred to the person administering the patch or a patient upon application of the predetermined threshold force. FIG. 11 illustrates an embodiment in which the microneedle patch 1100 has a base substrate 1120 that is coated on the microneedle side with a dye 1130 which is transferred to the patient's skin when a sufficient force is applied to the patch to cause the microneedles 1110 to be effectively inserted into the skin, such that the dye on the base substrate contacts and is transferred to the patient's skin. This dye transfer indicates proper/complete microneedle insertion.

Still other embodiments of mechanical force indicators may include a piezoelectric sensor or other electrical components. For example, a piezoelectric sensor may generate a voltage or current upon application of a predetermined threshold force. A transducer may be an integral part of the microneedle patch or may be attached to the backing layer or another component of the microneedle patch. An exemplary piezoelectric transducer may include a ceramic (e.g., barium titanate) sandwiched between two conductive plates or surfaces (e.g., copper). The transducer can be connected to a digital voltmeter or amp-meter to provide a voltage/current readout to signal whether a predetermined threshold force has been applied. The volt-/amp-meter may be an integral part of the microneedle patch or built into an applicator-like device that can be used to apply the microneedle patch. It also may be separate from the microneedle patch and connected to the piezoelectric transducer during administration of the microneedle patch.

In another embodiment, a microneedle patch may be configured such that an electrical circuit is completed upon application of the predetermined threshold. Two parallel, bendable conductive surfaces may be separated by an insulator, foam-like, or spring-like material, for example, shaped in a doughnut fashion. Upon application of the predetermined threshold force, the person applying the patch causes the upper conductive surface to bend and travel towards the lower conductive surface (as the insulator material is compressed between both conductive surfaces) until both conductive surfaces make contact and complete an electrical circuit that creates a signal (e.g., a light or a sound) that sufficient pressure was applied.

In another embodiment, an electrical circuit can be completed using the conductivity of liquid. The conductive liquid could be held within a capsule or blister incorporated into the patch that bursts upon application of the predetermined threshold force, releasing the conductive liquid to make the electrical connection between two electrodes. Alternatively, the conductive liquid could be from the skin or other tissue (e.g., interstitial fluid) that diffuses into the patch. The electrodes can be in the form of parallel plate electrodes that form a low-volume sensor, co-planar, or other suitable geometries. In either case, a sufficient volume of the conductive liquid is required to bridge both electrodes to complete the circuit and create a signal (e.g., a light or a sound) that sufficient pressure was applied.

In still other embodiments, a mechanical force indicator may be configured to create a particular tactile feedback to a user upon application of the predetermined threshold force. For example, upon applying the predetermined threshold force, a coldness/warmth or wetness may be produced from a material or object that is an integral part of or attached to the microneedle patch. In one embodiment, a material coated on the microneedle side of the base substrate triggers a sensation (e.g., heat, cold, etc.) when the microneedles fully puncture the patient's skin and the base substrate comes into contact with the patient's skin. Non-limiting examples of other types of tactile feedback include vibration, pain, hardness/softness, slickness/slipperiness, smoothness/roughness, softness/hardness, sharpness, pattern recognition, proprioception, kinesthesia, texture recognition, topagnosis, two-point discrimination, barognosis, and/or graphesthesia.

Microneedle Insertion, Dissolution, and Patch Wear Time

In another aspect, the feedback indicator provides information to the user (and/or patient) that (i) the microneedles have penetrated the skin and/or that the substance of interest has been released into the target tissue. Such indicators may be especially useful to provide a user confidence that the substance of interest was effectively delivered, particularly where delivery of the substance of interest is dependent upon insertion and dissolution of the microneedles or coating. The indicator may measure full or partial microneedle dissolution, depending on whether full or partial dissolution is needed for delivery of an effective amount of the substance of interest. For example, by measuring full dissolution, the indicator can signal to the user that the microneedle patch can be removed from the patient's skin.

It also may be useful in some circumstances for the indicator to signal partial dissolution if the partial dissolution would be sufficient to provide an effective amount of the substance of interest or to otherwise signal that user interaction with the microneedle patch is necessary or desirable. Another situation where detection of partial dissolution may be desirable is if multiple substances of interest are disposed in or coated onto the microneedles, with sequential release of the multiple substances of interest being provided by progressive dissolution. In such situations, it may be beneficial for a medical professional to be notified when each of the multiple substances of interest are released by an indicator that signals each of the various stages of dissolution.

In some embodiments, the indicator may signal or detect dissolution of individual microneedles or particular groups of microneedles (e.g., specific rows) within patch. Such an indicator could be useful if groups of microneedles are configured to be delivered at different times (e.g., to achieve controlled release of one or more substances of interest or if various microneedles are loaded with different substances of interest that it is desirable to release at different time points). In some embodiments, the indicator also may signal when the microneedles separate from the base substrate. Such embodiments would be appropriate for microneedles that are configured to separate from the base substrate upon insertion into the patient's skin or shortly thereafter, and would be advantageous where it is neither practical nor desirable to leave the patch on the patient's skin during dissolution of the microneedles, as may be the case of patients that are intentionally or unintentionally non-compliant.

One type of indicator for measuring insertion and/or dissolution of the microneedles is by the wetting of the backing layer (or other suitable layer) and/or diffusion of moisture in the backing layer. As used herein, "wetting" means an increase in liquid content. Typically, the wetting of the patch occurs after insertion of the microneedles into a tissue that contains fluid, with moisture from the skin, tissue, or interstitial fluid entering into the microneedles, backing layer, and/or other parts of the patch while the patch is inserted into and adhered to the tissue. The wetting may be detectable without an additional indicator or may trigger one or more changes in color, texture, shape, or the like. Often, the release of a substance of interest from the microneedles into the tissue is mediated at least in part by the entry of water into the microneedles. Such an indicator may be particularly beneficial for detecting whether all of the microneedles were partially or fully inserted, the substance of interest contained in the microneedles was successfully delivered, or the fluid/analyte was successfully collected (e.g., in the case of a diagnostics application, etc.), and/or as a measure of patch wear time (e.g., the patch becomes wetted after it has been applied to the skin/tissue for a time sufficient for the microneedles to dissolve or separate from the base).

In some embodiments, the wetting of the patch by interstitial fluid following insertion can be detected by a change in the refractive properties/index of the microneedles, rendering the microneedle insertion sites (holes) visible through a transparent microneedle patch (i.e., backing, body, adhesive, and base). The refractive change may include a lack of color (i.e., achromatic) to presence of a color (or vice versa), a weaker to a stronger color intensity (or vice versa), or a change of color (e.g., red to green). Such an indicator could be used to signal penetration of the microneedles, dissolution of the microneedles, and patch wear time.

Figure 9:
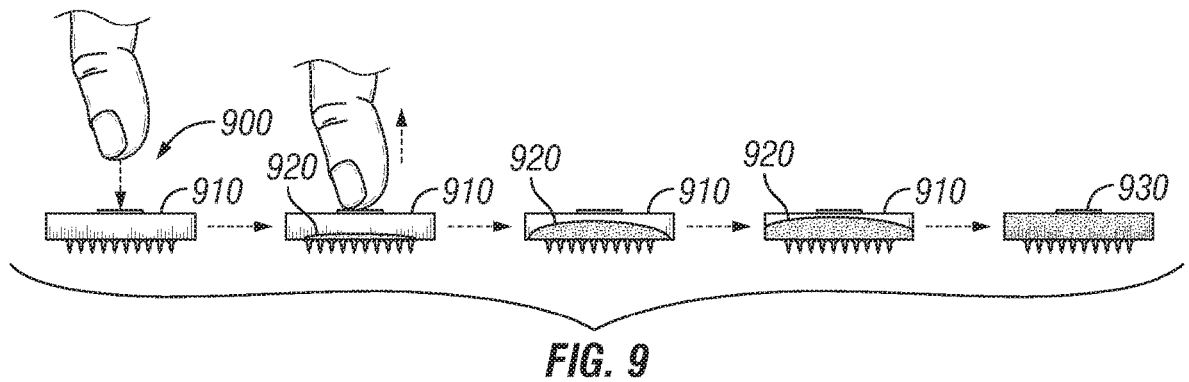

In an embodiment, the patch wear time required for effective administration of the substance of interest may be measured by a diffusive indicator whose length is equal to or longer than an expected time of delivery. The diffusive indicator may be triggered by moisture from the skin, tissue, and/or interstitial fluid, such that once the patch is applied to tissue, or shortly thereafter, the diffusive process starts. The diffusive indicator also may be triggered mechanically, for example, by application of pressure on the patch during its application to release a fluid in the patch, or by some other means once the patch is applied (see FIG. 10). An exemplary embodiment of a microneedle patch 900 including a diffusive indicator in an upper surface 910 of the patch 900 is illustrated in FIG. 9. In FIG. 9, fluid 920 from the skin begins to enter the patch 900 upon application of the patch 900 to the skin. Over time, fluid 920 moves through the patch 900 and the upper surface 910 of the patch where it comes into contact with a color indicator 930, providing a signal in the form of a color change induced by the fluid 920 contacting a color indicator 930.

Another diffusive indicator that may be used to signal microneedle penetration, dissolution, and/or patch wear time may involve a chemical reaction. For example, once the diffusion process occurs, a chemical reaction occurs to provide a detectable signal (e.g., a color change). Alternatively, the chemical reaction may be diffusion controlled or otherwise have a delayed onset (e.g., by fluid diffusing to contact a chemical reactant). Such chemical reactions also may be triggered, at least in part, by a mechanical trigger that releases the chemical reactant following rupture of a reservoir containing the chemical reactant, similar to the above-described mechanisms involving a dye.

In some embodiments, the chemical reaction may have a reaction time that is equal to (or longer than) the desired patch wear time. The reaction may be triggered at the time the patch is removed from its packaging (e.g., oxidation from exposure to air) or at the time it is applied to the skin (e.g., wetting of the patch). Another embodiment may include a chemical reaction that is triggered by removal of a component of the patch before or after application of the patch to the patient's skin (e.g., following removal of a release liner to expose a chemical reactant to air or light).

Another indicator that may be used to detect penetration and/or dissolution of the microneedles and/or patch wear time may include release of a dye onto a tissue (e.g., skin) or into surrounding tissue. For example, the dye may be encapsulated inside the microneedles or coating such that the dye is released upon the dissolution of the microneedles or coating. In some embodiments, the dye may change color when released from the microneedles into the tissue (e.g., may have no color when in the microneedles and change color when released or vice versa). In some embodiments, the dye may not change color, but may not be visible in the microneedles and become visible once released from the microneedles. Because of the microneedle's size, a dye or other colorant loaded disposed in the microneedles and/or a coating may not be very visible to the naked eye; however, the release and spread of the dye into the tissue upon dissolution of the microneedles becomes much more visible and obvious to the naked eye.

Similarly, in embodiments, the dissolution of the microneedles or coating and release of the substance of interest also can be measured indirectly, for example, by detecting or observing an effect of the administered substance of interest or by detecting or observing the release of a surrogate for the substance of interest. For example, if the actual release of the substance of interest cannot be detected or measured, the indicator may be designed to detect or measure the release of a surrogate substance (e.g., included in the microneedle, the release of which correlates with the release of the substance of interest). For another example, the dissolution of the microneedles or drug coating may be measured by a specific local or systemic effect/sensation/feeling or a change that can be detected by the patient and/or a person administering the patch (e.g., skin color change in the case of a substance of interest with vasoconstrictive properties).

In another embodiment, an indicator may be used to detect patch wear time may include a dye that evaporates or fades during administration of the patch. For example, a dye may be used to print text or an image on the backing layer of the patch. A protective layer disposed over the text or image may be covered with a protective layer to prevent its evaporation or fading prior to administration. After application of the patch to a patient's skin, the protective layer may be removed (e.g., peeled off) to expose the dye. The dye or ink may be configured to evaporate or fade (e.g., due to oxidation or exposure to light) over a certain amount of time. Thus, the disappearance of the dye signals that the patch can be removed from the skin.

Integrity and Storage of Microneedles

Indicators also can be provided to detect the integrity of the microneedles following storage and shipping, including the measuring the temperature, humidity, or vibrations/force that the patch has been exposed during storage and shipping. Such indicators can be integrated into the patch itself and/or the packaging. Such indicators may be useful to determine whether the patch was stored at appropriate conditions before being used, as the functionality and stability of the substance of interest and the integrity of the microneedles may be adversely affected if the patch is exposed to deleterious conditions (e.g., extreme temperatures, humidity, or vibrations/force).

In embodiments, an indicator for measuring the storage temperature may include a vaccine vial monitor (VVM) or similar technology that will provide a signal (e.g., change of color) if exposed to excessive temperature over time. The VVM can be integrated within the patch packaging or the patch itself (e.g., part of the backing layer). In some embodiments, the indicator may be in the form of a thermochromic material, and is a component of or applied as a sticker to the backing layer or patch packaging. The VVM or similar technology may be used to detect exposure to a threshold temperature at or above which damage to the substance of interest will occur or integrated time-temperature exposure where both the exposure time and the temperature(s) to which the patch is exposed are taken into consideration. Integrated time-temperature exposure may be assessed via a material phase change, a chemical reaction, an electronic device and other methods known in the art.

In embodiments, an indicator for measuring the level of humidity a patch is exposed to during storage and transport may be assessed using humidity indicating dyes. Such dyes change color due to exposure to certain humidity levels, and may be incorporated within the patch or patch packaging. For example, the humidity indicator may be in the form of a card that shows a number of humidity ranges or just a single spot that changes color if the humidity rises above a certain threshold. Such cards may be based on cobalt (II) chloride base, copper (II) chloride base, or similar chemistry. Alternatively, the humidity indicator may be incorporated within desiccant included in the packaging that is visible to the user or healthcare provider prior to application of the patch. Humidity indicators also may be measured using an electronic devices (e.g., a humidity meter) that are an integral part of the patch or packaging; or by a water-sensitive degradation, reaction, or phase change; by hygroscopic and/or deliquescent material (e.g., material that will readily absorb moisture and undergo some reaction or some other physical change). Non-limiting examples of deliquescent materials include salts (e.g., calcium chloride, magnesium chloride, zinc chloride, potassium carbonate, potassium phosphate, carnallite, ferric ammonium citrate, potassium hydroxide, and sodium hydroxide), and some sugars that undergo a phase change from solid to liquid upon absorption of moisture from air.

In embodiments, indicators for detecting excessive vibration/force may include a component of the patch or packaging (e.g., a protective cap) configured to collapse and deform or break if it is subjected to a force that would otherwise compromise the structural integrity of microneedles or any other component of the patch. In another embodiment, an accelerometer or shock and drop indicator may be incorporated into the patch or its packaging to detect vibration or shock the microneedle patch may be subjected to during storage and/or transport. A shock and drop indicator will activate when an impact level exceeds a predetermined level (level that will compromise the microneedle patch), and may be in the form of a device with a specific sensitivity or in the form of go/no-go device that indicates whether the patch packaging has been dropped during storage or transport.

It will be appreciated from the foregoing that certain indicators advantageously may be capable of providing multiple forms of feedback. For example, a snap dome can be used to provide feedback about the pressure applied to patch, wear time and/or dissolution (e.g., by delayed reversibility of deformation), and/or patch exhaustion/use (e.g., by irreversible deformation). A mechanical force indicator including a reservoir of dye can be used to provide feedback about the pressure applied to the patch during use, wear time and/or dissolution (e.g., by diffusion of the dye), patch exhaustion/use (e.g., by change of color), and/or exposure to extreme vibrations/force during shipping and handling (e.g., if the reservoir is ruptured prior to use such that the dye is released into the patch or within the patch packaging).

The above-described indicators also may be used to provide other types of signals and feedback. For example, one or more indicators that provide feedback that the patch has been removed from its packaging or administered may trigger an authorization of payment for treatment. In another embodiment, one or more indicators that provide feedback that the patch has been successfully administered may be used to verify compliance with a requirement that the patient undergo treatment (e.g., a school, employer, government, or military requirement for certain vaccinations/treatments). In an embodiment, one or more indicators that provide feedback of successful patch administration may be used to protect healthcare providers, manufactures, and distributors from liability. In an embodiment, one or more indicators that provide feedback regarding various aspects of the patch administration may be used by the manufacturer or healthcare provider to modify the design or administration of the patch or to aid with logistics relating to supply of the patch (e.g., when and how many patches to manufacture and distribute).

Substance of Interest/Active Pharmaceutical Ingredient

A wide range of substances may be formulated for delivery to biological tissues with the present microneedle patches and methods. As used herein, the term "substance of interest" includes active pharmaceutical ingredients, allergens, vitamins, cosmetic agents, cosmeceuticals, markers (e.g., colored dyes or radiological dyes or markers), and other materials that are desirable to introduce into a biological tissue, in particular into a tissue of a human or other mammal, including but not limited to the skin of human or other mammal. In an alternative embodiment, the biological tissue is a plant tissue.

In one embodiment, the substance of interest is a prophylactic, therapeutic, or diagnostic agent useful in medical or veterinary applications. In one embodiment, the substance of interest is a prophylactic or therapeutic substance, which may be referred to herein as an API. In certain embodiments, the API is selected from suitable proteins, peptides and fragments thereof, which can be naturally occurring, synthesized or recombinantly produced. Representative examples of types of API for delivery include antibiotics, antiviral agents, analgesics, anesthetics, antihistamines, anti-inflammatory agents, anti-coagulants, allergens, vitamins, antineoplastic agents, antigens, and toxins. In one embodiment, the substance of interest comprises a vaccine.

A microneedle patch may include a single substance of interest or it may include two or more substances of interest. In the latter case, the different substances may be provided together within one of the microneedles, or some microneedles in an array of microneedles contain one substance of interest while other microneedles in the array contain another substance of interest.

The API desirably is provided in a stable formulation or composition (i.e., one in which the biologically active material therein essentially retains its physical stability and/or chemical stability and/or biological activity upon storage). Stability can be measured at a selected temperature for a selected period. Trend analysis can be used to estimate an expected shelf life before a material has actually been in storage for that time period.

In embodiments, the substance of interest is provided as a solid that is "dry" or has been "dried" to form (e.g., in combination with a matrix material) at least a portion of the one or more microneedles or a portion of a coating on a microneedle sub-structure that becomes solubilized in vivo following insertion of the microneedle into the patient's biological tissue.

As used herein, the term "dry" or "dried" refers to a composition from which a substantial portion of any water has been removed to produce a solid phase of the composition. The term does not require the complete absence of moisture (i.e., the API may have a moisture content from about 0.1% by weight and about 25% by weight).

The substance of interest may be included in a formulation with one or more excipients and other additives that are used in pharmaceutical formulations. Non-limiting examples of such excipients include stabilizers, buffers, bulking agents or fillers, adjuvants, surfactants, disintegrants, antioxidants, solubilizers, lyo-protectants, antimicrobials, antiadherents, colors, lubricants, viscosity enhancer, glidants, preservatives, materials for prolonging or controlling delivery (e.g., biodegradable polymers, gels, depot forming materials, and others). The excipients may be FDA approved excipients (such as those listed in the FDA's Inactive Ingredient Search for Approved Drug Products) or may be novel, and may be effective to perform more than one function (e.g., a sugar may be used as a stabilizer and a bulking agent, a buffer may be used to both buffer pH and protect the substance of interest from oxidation). The one or more selected excipients desirably improve the stability of the substance of interest during drying and storage of the microneedle patches.

Methods of Use

The microneedle patches provided herein may be self-administered or administered by another individual (e.g., a parent, guardian, minimally trained healthcare worker, expertly trained healthcare worker, and/or others). Unlike prior art microneedle systems, the microneedle patches provided herein may be directly handled and administered by the person applying the patch without requiring use of an applicator to apply the required force/pressure, thereby allowing for a very simple, low-profile (i.e., thin and patch-like) microneedle patch.

Thus, embodiments provided herein further include a simple and effective method of administering a substance of interest with a microneedle patch, illustrated in part in FIGS. 13A-13D. The method may include identifying an application site and, preferably, sanitizing the area prior to application of the microneedle patch (e.g., using an alcohol wipe). If needed, the application site may be allowed to dry before application of the microneedle patch. The patch may be removed from the tray in which it is releasably secured by grasping the tab portion of the patch between the thumb and finger and peeling the patch from tray. The patch then is applied to the patient's skin/tissue and manually pressed into the patient's skin/tissue (e.g., using the thumb or finger) by applying a sufficient pressure to insert the one or more microneedles into the patient's skin/tissue. After administration is complete, the patch may be removed from the patient's skin/tissue by manually grasping the tab portion (e.g., between the thumb and finger), peeling the patch off the patient's skin/tissue, and discarding the patch.

In some embodiments, a user may use one or more indicators prior to, during, and/or after administration of the microneedle patch. Such indicators may be elements incorporated into the microneedle patch that provide a detectable signal or may result from the user performing one or more actions, such as evaluating the microneedle patch or patient's skin/tissue following administration. Although such indicators may be passive (e.g., providing the signal without user engagement, such as by the diffusive mechanisms described above), such indicators also may be active (e.g., requiring user engagement), or may be a combination of passive and active. For example, assessment of indicators at the patch level may be characterized as an "overall assessment", whereas assessments made to the patch and/or skin/tissue by the user may be characterized as a "regional assessment" (e.g., detection of a signal generated by the microneedle patch would be a passive, overall assessment, whereas inspection of microneedles following administration of the patch would be an active, regional assessment).

Various indicators may be assessed by a user during application of the patch to signal whether the patch has been properly applied and/or may be removed. For example, in some embodiments an indicator provides a signal that a predetermined threshold force has been reached or that the microneedles have penetrated/punctured the patient's skin, indicating that the user may discontinue applying pressure to the patch. Optionally, the signal may provide an indication that the user should continue applying the pressure for an additional specified time (e.g., several seconds) prior to releasing the pressure. In some embodiments, another indicator provides a signal that administration is complete, indicating that the user may remove the patch from the patient's skin/tissue. For example, the indicator may provide a signal that specified time period has passed or that the microneedles or coating have dissolved.

Indicators that provide a user with a signal that a sufficient period of time has passed after applying the patch to the patient's skin/tissue can provide a user with confidence that the substance of interest has been successfully administered prior to removing the patch from the patient's skin/tissue. This is especially useful in situations where monitoring (e.g., measuring) the patch wear time is not possible, practical, or desirable by the user and/or patient. For example, a healthcare provider responsible for applying patches to multiple individuals at different times would be able to apply the patch to multiple individuals while checking at various time intervals whether the indicator signals that the patch wear time has lapsed and/or the substance of interest has dissolved. In this way, the healthcare provider can provide care to multiple individuals during a given time period without having to provide individualized attention to each patient during the entire administration period. Such an indicator also would provide a signal to the patient that the patch could be removed by the healthcare provider or by the patient him/herself (or guardian) after leaving the doctor's office/clinic, or after administration outside the clinic (e.g., at home).

In addition to the above-described embodiments of indicators that may be effective to determine whether a sufficient period of time has passed for successful administration of the substance of interest, another indicator may include a clock, stopwatch, or other timing device (e.g., optionally with an alarm to signal when a predetermined time period has passed) integrally formed with the patch. In another embodiment, the patch may include a backing layer onto which a user may write the time at which the patch was applied or the time at which the patch may be removed directly on the patch (or on any associated papers or packaging).

Other types of feedback also may be used to determine whether a sufficient period of time has elapsed and/or whether the microneedles have successfully penetrated the skin/tissue or dissolved. For example, passage of a predetermined time period may be detected by an increase in the temperature of the microneedle patch (e.g., as determined via tactile feedback or via a thermometer or other temperature-sensing mechanism that may be integral with the patch) for those instances in which a chilled microneedle patch that is refrigerated during storage increase temperature following application onto a patient's skin/tissue.

Another type of feedback that a user may consider in evaluating whether a sufficient period of time has passed and administration of the microneedle patch is complete includes the ability of the user to move the patch on the skin/tissue surface. The microneedles inserted into the skin/tissue act as anchors for the microneedle patch. Once the microneedles are dissolved, the patch is less anchored to the skin/tissue surface and can be more readily moved. Thus, an ability to move the patch on the skin/tissue surface can be used to provide feedback that the microneedles have dissolved and the patch may be removed from the patient's skin/tissue.

The quality or success of the microneedle administration also may be evaluated via other types of feedback after removal of the microneedle patch, for example, by inspection of the patch or patient's skin/tissue. In an embodiment, feedback may be provided by evaluating the depth of microneedle penetration by the presence or absence of blood on the surface of the skin/tissue or in the holes formed by the microneedles (e.g., shallow insertion typically results in no or less blood being present, while deeper insertion is more likely to puncture the capillaries in the dermis to produce more blood). In another embodiment, feedback may be provided by a dye contained in the patch that is configured to stain the viable epidermis and/or upper dermis (or other tissue) at the puncture sites, such that a pattern of dye remains following washing away the excess dye. In still another embodiment, feedback of successful penetration may be provided by evaluating a film applied onto the application site where the patch is to be applied. Following application and removal of the patch, the film can be inspected for any signs of puncture either while on the skin or after peeling it off the skin/tissue. In some embodiments, the film may be configured such that a threshold force must be applied to pierce the film, the threshold force being sufficient for the microneedles to also pierce the skin/tissue.

Feedback of microneedle penetration also may be gauged by measuring the electrical resistance of skin, as a drop in resistance or a specific change in resistance indicates puncture of the stratum corneum and may be detected via either an electrode included in the patch or by using a separate device to probe the application site after patch removal.

In still another embodiment, feedback may be provided by examining the microneedle patch following administration. For example, the amount of the microneedles that dissolved (e.g., complete or partial dissolution) is a direct indication of the insertion depth. Therefore, if a portion of a microneedle did not dissolve, it is likely that this portion was not inserted into skin or did not remain inserted long enough to dissolve sufficiently. Conversely, if the entire microneedle or a substantial majority of the microneedle is gone after use, it is likely an indication that the microneedle was completely or substantially dissolved and the substance of interest was successfully administered. Similarly, if the microneedles included a dye and the patch lacked that dye after administration, the absence of that dye would be an indication that the microneedle was completely dissolved and the substance of interest was successfully administered. Alternatively, different colors associated with different parts of the microneedle (i.e., for partial dissolution) may be used to identify whether the desired portion of the microneedle was successfully administered.

Using the above-described indicators and feedback, a user will be able to determine whether a patch has been successfully administered and will be able to make an appropriate decision if it is determined that the microneedle patch was not properly administered. For example, a user may be able to increase the pressure applied to the patch so that the microneedles penetrate the skin/tissue or may determine that another patch can or should be administered.

The above-described indicators and feedback also may function to provide evidence that the microneedle patch has already been used, and may be helpful in situations in which the patch is not properly discarded after use (i.e., thereby avoiding attempts to reuse the patch, which would result in an ineffective treatment, or potential exposure to a biohazardous material that has been contaminated by the previous patient's bodily fluids). Evidence of use of microneedle patches is particularly helpful because the microneedles are such small structures that are barely visible with the naked eye.

Additional elements also may be included in the patch or additional steps may be taken during administration to provide such feedback. For example, a dye or other material may be applied to skin/tissue prior to application of the patch and at least a portion of the dye or other material may transfer to the patch during its administration, thereby indicating that the patch has been used. The microneedle patch also may be folded together after its use or placed back into its packaging (i.e., placed back in its tray) for disposal. Alternatively, the microneedle patch and/or its packaging may be configured to be torn or otherwise partially or fully separated into multiple pieces following administration.

Manufacture

Methods for manufacturing microneedle patches and systems also are provided. Such methods preferably are performed under a minimum ISO 7 (class 10,000) process or an ISO 5 (class 100) process.

In one embodiment, the manufacture of solid, dissolvable microneedles includes filling a negative mold of the one or more microneedles with an aqueous or non-aqueous casting solution of the substance of interest and drying the casting solution to provide the one or more solid microneedles. In other embodiments, other solvent or solventless systems may be used. Non-limiting examples of methods for filling the negative mold include deposition, coating, printing, spraying, and microfilling techniques. The casting solution may be dried at ambient temperature for a period from about 30 minutes to about one week to form the dry solid microneedles (e.g., from about 45 minutes to about one week, from about one hour to about one week, from about one hour to about one day, etc.).

Alternatively, the casting solution may be vacuum-filled or filled into the mold using a combination of non-vacuum filling and vacuum-filling. For example, in an embodiment the negative mold comprises a non-porous but gas-permeable material (e.g., PDMS) through which a backside vacuum can be applied. Although the negative mold is solid, it was determined that a sufficient vacuum could be applied through the backside when the molds are formed of such materials. In some embodiments, the backside vacuum may be used alone or in combination with a positive pressure applied on top of the mold. Such embodiments could advantageously reduce the time required and improve the accuracy and completeness when filling the mold with casting solution. For example, the casting solution may be vacuum-filled using a backside vacuum for a period from about 3 minutes to about 6 hours, from about 3 minutes to about 3 hours, from about 3 minutes to about 1 hour, or from about 3 minutes to about 30 minutes.

Although various temperatures and humidity levels can be employed to dry the casting solution, the formulations preferably are dried at temperature from about 1° C. to about 150° C. (e.g., from about 5° C. to about 99° C., from about 15° C. to about 45° C., from about 25° C. to about 45° C., or at about ambient temperature) and about 0 to about 20% relative humidity.

In some embodiments, it may be desirable to use a multi-step casting process to form the microneedles and base substrate. For example, the tips of the microneedles may be partially filled in a first step with a casting solution comprising the substance of interest followed by one or more subsequent fill steps with casting solutions of bulking polymers with or without the same or a different substance of interest. After filling and at least partially drying the microneedles in the negative mold, the adhesive layer and backing layer may be applied to the base substrate prior to removing the microneedles from the mold. In some embodiments, the adhesive layer and/or backing layer are pre-formed prior to application to the base substrate, while in other embodiments the adhesive layer and/or backing layer may be formed directly in-line. The patch may optionally also include an indicator and/or a separate tab portion incorporated into the patch.

After at least partially drying the microneedles, the microneedles may be removed from the mold. For example, the microneedles may be removed from the mold before fully dry (e.g., when still in a rubbery state), but when strong enough to be peeled, and then dried further once removed from the mold to further solidify/harden the microneedles. Such a technique may be useful when carboxymethylcellulose sodium, polyvinyl alcohol, sugars, and other materials are used as a bulking polymer (matrix material) in the microneedles. In such embodiments, the microneedles may complete drying prior to or after packaging.

The microneedle patches may then be attached to the trays and undergo one or more additional packaging steps. For example, the microneedle patches may be applied to the tray and packed in a foil pouch with desiccant, preferably under aseptic conditions. The foil pouches containing the microneedle patches and trays may then be removed from the aceptic conditions to be further packaged in cardboard boxes prior to being stored. The storage conditions will depend in part on the thermal stability of the substance of interest. For example, the microneedle patches may require storage under refrigeration, for example at temperatures from about 2° C. to about 8° C.; in a freezer, for example at temperatures below 0° C.; at ambient temperature; or at uncontrolled temperature, for example up to 50° C. The storage may be for the shelf life of the product or for a period less than the shelf life of the product.

Although the above process is described with reference to manufacturing a single microneedle patch, the negative molds may be configured to form a plurality of microneedle patches. For example, in embodiments the negative mold may be configured to produce 6 or more patches, 12 or more patches, and the like.

The microneedle patches, systems, and methods may be further understood with the following non-limiting examples.

Example 1: Fabrication of Microneedle Patches with Mechanical Force Indicator

Etched, stainless steel microneedles were mounted on adhesive foam backing (TM9942, MacTac, Stow, Ohio) and packaged with polyacetal. Each patch contained 50 hexagonally-packed microneedles, 750 µm long, with a row spacing and column spacing of 1.6 and 1.0 mm, respectively. Parts were assembled with double sided adhesive (1522, 3M, Minneapolis, Minn.) and sent for ethylene oxide sterilization.

A mechanical force indicator was fabricated to facilitate microneedle insertion. A resistive strain gauge load cell (RSP1-010M-A, Loadstar Sensors, Fremont, Calif.) was used to evaluate these devices compared to the force an experienced, blinded investigator uses to insert microneedle patches. The mechanical force indicators were constructed from polypropylene screw caps (91620A200, McMaster-Carr, Atlanta, Ga.), cardstock paper, and double-sided tape (1522, 3M, Minneapolis, Minn.). Tape was applied to the cardstock paper, cut into 14 mm circles, and applied to the bottom of the device. The paper was applied to cover a hole that exists in the caps to ensure that even force was applied across the bottom of the device.

A study was carried out to evaluate use of the mechanical force indicators. The mechanical force indicators were packaged separately from the patches, and the indicators were applied to patches during administration procedures. First, a patch would be placed on a human participant's arm with the microneedles facing down. The adhesive would hold the patch in place. Then, the participant would take a mechanical force indicator from the investigator and place a device over the microneedle array. The participant would then press the hinged lid closed while keeping the device positioned over the needle array. When the mechanical force indicator closed and made a clicking noise, the participant would throw the device away.

The participants in the study were given the following verbal instructions for use of the patch with the mechanical force indicator:

Open the pouch. Peel away the blue plastic film. Pick up the patch without touching the metal part (i.e., the microneedles).

Peel the foam part off the hard plastic part (i.e., the microneedle patch packaging).

Put the patch on your arm. Place it metal side down on a part of your forearm with the least amount of hair.

Place the mechanical force indicator directly above the metal part of the patch.

Clinch your fist. Keep the mechanical force indicator in place and press it closed until you hear a clicking noise.

The volume of the clicking noise was measured. At a distance of 15.2 cm, the closing snap produced a sound intensity of 71±1.2 dB (n=6, Sound Meter v.1.5.4 for Android devices, Smart Tools Co.). This is approximately 12 times louder than normal conversation, 60 dB. At 45 cm, which is a better approximation of the distance from ear to volar forearm, the sound intensity should be approximately 62 dB, since sound intensity dissipates by the ratio of distances squared.

The study determined if participants could apply microneedle patches with minimal training. Subjects self-administered placebo microneedle patches three times, had a placebo microneedle patch administered by study personnel and received an IM injection of saline in randomized order. Participants were well distributed in terms physical and socioeconomic factors. The microneedle patch with the mechanical force indicator made a snapping sound when a force of approximately 37 N was applied.

The results of the study were analyzed. Without the mechanical force indicator, the median number of insertion sites of microneedles puncturing into the skin observed on the first attempt by subjects to self-administer was 90%. The variability between participants was high with an interquartile range (IQR) of 44%. On the second and third attempt, the median number of insertion sites observed increased to 94% and the variability decreased (IQR: 13-15%). The improvement in administration success was statistically significant ($p=0.003$, $n=57$, Friedman's rank test), indicating a learning curve. This suggested the need for a device to assist with microneedle insertion.

With the mechanical force indicator, the median number of insertion sites observed on the first attempt was 96%, and the variability between subjects was lower than before (IQR: 5%). The improvement in the number of insertion sites observed on the first attempt was statistically significant ($p=0.006$, Mann-Whitney U). The second and third attempts performed similarly well (median percent inserted: 93-95%, IQR: 9-10%). This shows that a mechanical force indicator that provides feedback to the user regarding insertion force improved microneedle insertion success.

While the invention has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereof.

We claim:

1. A microneedle patch for administration of a substance of interest into a biological tissue, the microneedle patch comprising:
a base substrate having a microneedle side and an opposing back side;
solid microneedles extending from the microneedle side of the base substrate, the solid microneedles being formed of a composition which comprises (i) a substance of interest selected from active pharmaceutical ingredients, allergens, vitamins, cosmetic agents, cosmeceuticals, and markers, and (ii) a water-soluble matrix material in which the substance of interest is dispersed;
an indicator connected to the opposing back side of the base substrate, wherein the indicator is configured to provide an audible, tactile, and/or visual signal when a force applied to the patch by a user, in the course of applying the patch to a biological tissue to insert the solid microneedles into the biological tissue, meets or exceeds a predetermined threshold;
a handle layer affixed to the base substrate and including an elongated tab portion extending laterally away from the solid microneedles, the tab portion being configured for manual manipulation of the patch; and
an adhesive layer which comprises (i) a first adhesive composition disposed between and securing together the base substrate and the handle layer, and (ii) a second adhesive composition disposed on the handle layer beyond the base substrate and configured to releasably secure the patch to the biological tissue.

2. A microneedle patch comprising:
a base substrate having a microneedle side and an opposing back side;
an array of solid microneedles extending from the microneedle side of the base substrate, the solid microneedles being formed of a composition which comprises an active pharmaceutical ingredient, and a water-soluble matrix material in which the active pharmaceutical ingredient is dispersed;
an indicator connected to the opposing back side of the base substrate, wherein the indicator is configured to provide an audible, tactile, and visual signal when a force applied to the patch by a user, in the course of applying the patch to a biological tissue to insert the solid microneedles into the biological tissue, meets or exceeds a predetermined threshold;
a handle layer affixed to the base substrate and including an elongated tab portion extending laterally away from one side of the solid microneedles, the tab portion being configured for manual manipulation of the patch; and
an adhesive layer disposed between and securing together the base substrate and the handle layer.

3. The patch of claim 2, wherein the adhesive layer extends beyond the base substrate and is configured to adhere the patch to the biological tissue and/or to a storage tray.

4. The patch of claim 3, further comprising a tray having a recessed region dimensioned to receive in a non-contacting manner the microneedles, with the adhesive layer releasably secured to an upper surface region of the tray.

5. The patch of claim 4, wherein the tray has a partial ellipsoidal shape and part of the tab portion extends beyond a perimeter of the tray.

6. The patch of claim 1, wherein the first adhesive composition has a coefficient of adhesion between the base substrate and the handle layer that is greater than the coefficient of adhesion of the second adhesive composition between the handle layer and a patient's skin.

7. The patch of claim 1, wherein the indicator is a mechanical force indicator which comprises a button that is deformed and/or displaced when the force applied to the patch meets or exceeds the predetermined threshold.

8. The patch of claim 7, wherein the mechanical force indicator comprises a snap dome disposed inside a housing.

9. The patch of claim 7, wherein the mechanical force indicator is integrated with another component such that the displacement is irreversible when the force applied to the patch meets or exceeds the predetermined threshold.

10. The patch of claim 9, wherein the another component comprises a snap-in-place mechanism or latch.

11. The patch of claim 1, wherein the substance of interest comprises a vaccine or other active pharmaceutical ingredient, and the solid microneedles have a height from about 100 μm to about 2000 μm.

12. A microneedle patch for administration of a substance of interest into a biological tissue, the microneedle patch comprising:
a base substrate having a microneedle side and an opposing back side;
solid microneedles extending from the microneedle side of the base substrate, the solid microneedles being formed of or coated with a composition which comprises a substance of interest selected from active pharmaceutical ingredients, allergens, vitamins, cosmetic agents, cosmeceuticals, and markers; and
an indicator which comprises:
an indicator housing affixed to the opposing backside, and
a mechanical force indicator disposed inside the housing and configured to provide an audible, tactile, and visual signal when a force applied to the patch by a user, in the course of applying the patch to a biological tissue to insert the solid microneedles into the biological tissue, meets or exceeds a predetermined threshold,
wherein the mechanical force indicator is in line with and generally centered about the solid microneedles on the opposing back side of the base substrate,
wherein the mechanical force indicator has:
an initial configuration before providing the audible, tactile, and/or visual signal, and
a signaling configuration which differs from the initial configuration and which provides, or which the transition thereto provides, the audible, tactile, and/or visual signal, and
wherein the mechanical force indicator changes from the initial configuration to the signaling configuration upon receiving a force which meets or exceeds the predetermined threshold, and wherein the change from the initial configuration to the signaling configuration is irreversible upon removal of the force which meets or exceeds the predetermined threshold.

13. The patch of claim 12, wherein the mechanical force indicator has a dome or other non-planar shape when in the initial configuration.

14. The patch of claim 13, wherein the mechanical force indicator is metal.

15. The patch of claim 12, further comprising:
a handle layer affixed to the base substrate and including an elongated tab portion extending laterally away from one side of the solid microneedles, the tab portion being configured for manual manipulation of the patch; and an adhesive layer disposed between and securing together the base substrate and the handle layer.

16. The patch of claim 15, wherein the adhesive layer extends beyond the base substrate and is configured to adhere the patch to the biological tissue and/or to a storage tray.

17. The patch of claim 16, further comprising a tray having a recessed region dimensioned to receive in a non-contacting manner the microneedles, with the adhesive layer releasably secured to an upper surface region of the tray.

18. The patch of claim 12, wherein the composition further comprises a water-soluble matrix material in which the substance of interest is dispersed, and wherein the solid microneedles are formed of the composition.

19. The patch of claim 12, wherein the substance of interest comprises a vaccine or other active pharmaceutical ingredient, and the solid microneedles have a height from about 100 μm to about 2000 μm.

20. The patch of claim 12, further comprising an adhesive layer affixing the indicator to the base substrate.

21. A microneedle patch for administration of a therapeutic or prophylactic agent into a patient's skin, the microneedle patch comprising:
   a base substrate having a microneedle side and an opposing back side;
   dissolvable microneedles extending from the microneedle side of the base substrate, the dissolvable microneedles being formed of a composition comprising a water-soluble matrix material in which the therapeutic or prophylactic agent is dispersed;
   a snap dome which is connected to the opposing back side of the base substrate and which is configured to deform when a force applied to the patch by a user, in the course of applying the patch to the skin to insert the dissolvable microneedles into the skin, meets or exceeds a predetermined threshold, to produce an audible, tactile, and visual signal indicative, to the user, of insertion of the dissolvable microneedles into the skin;
   a handle layer affixed to the base substrate and including an elongated tab portion extending laterally away from one side of the dissolvable microneedles, the tab portion being configured for manual manipulation of the patch; and
   an adhesive layer disposed between and securing together the base substrate and the handle layer,
   wherein the adhesive layer extends beyond the base substrate and is configured to adhere the patch to the skin and/or to a storage tray.

22. The patch of claim 21, further comprising a tray having a recessed region dimensioned to receive in a non-contacting manner the microneedles, with the adhesive layer releasably secured to an upper surface region of the tray with part of the tab portion extending beyond a perimeter of the tray.

23. A system for storing and transporting one or more microneedle patches comprising:
   one or more of the microneedle patches of claim 2; and
   a tray comprising an upper surface region surrounding one or more recessed regions,
   wherein each of the one or more recessed regions is dimensioned to receive in a non-contacting manner the solid microneedles of a corresponding microneedle patch, with a portion of the adhesive layer of the microneedle patch being releasably secured to the upper surface region of the tray, and
   wherein the upper surface region comprises a material having a surface energy of up to about 30 dynes/cm.

24. A system for storing and transporting one or more microneedle patches comprising:
   one or more of the microneedle patches of claim 2; and
   a tray comprising an upper surface region surrounding one or more recessed regions,
   wherein each of the one or more recessed regions is dimensioned to receive in a non-contacting manner the solid microneedles of a corresponding microneedle patch, with a portion of the adhesive layer of the microneedle patch being releasably secured to the upper surface region of the tray, and
   wherein the tray comprises a formed cap.

25. A method of administering a substance of interest into a biological tissue, the method comprising:
   providing the microneedle patch of claim 2 in a tray;
   removing the microneedle patch from the tray by grasping the tab portion of the microneedle patch;
   applying the microneedle patch, following its removal from the tray, to the biological tissue; and
   manually pressing the microneedle patch to apply a pressure effective to insert the microneedles into the biological tissue.

26. The method of claim 25, wherein, when the microneedle patch is manually pressed with a force that meets or exceeds a predetermined threshold, the indicator produces an audible, tactile, and/or visual signal.

27. The method of claim 25, wherein, after being applied to the biological tissue, the indicator provides an audible, tactile, or visual signal indicative of completion of delivery of the substance of interest.

28. The method of claim 27, wherein the audible, tactile, or visual signal indicative of completion of delivery of the substance of interest is provided by an indicator which comprises a reservoir containing a dye, which is released or changes position after a period effective to complete in vivo dissolution of the microneedles.

29. A microneedle patch comprising:
   a base substrate having a microneedle side and an opposing back side;
   an array of microneedles extending from the microneedle side of the base substrate, the solid microneedles being formed of a composition which comprises (i) a therapeutic or prophylactic agent, and (ii) a matrix material in which the substance of interest is dispersed;
   a mechanical force indicator attached to the opposing back side of the base substrate, the mechanical force indicator being configured to provide audible, tactile, and visual indications when a force has been applied to the patch that meets or exceeds a predetermined threshold; and
   a handle layer affixed to the base substrate and including an elongated tab portion extending laterally away from the solid microneedles, the tab portion being configured for manual manipulation of the patch, wherein the mechanical force indicator comprises a button that is irreversibly displaced when the force applied to the patch meets or exceeds the predetermined threshold.

30. The microneedle patch of claim 29, wherein the microneedles are dissolvable.

31. The microneedle patch of claim 29, wherein the microneedles are configured to separate from the base substrate.

* * * * *